US005910418A

United States Patent [19]
Hill et al.

[11] Patent Number: 5,910,418
[45] Date of Patent: Jun. 8, 1999

[54] ANTIBODIES AND ASSAY FOR DETECTING MUTANT APC PROTEINS

[75] Inventors: David E. Hill, Arlington; Karen A. Johnson, Watertown, both of Mass.; Kenneth W. Kinzler; Bert Vogelstein, both of Baltimore, Md.

[73] Assignee: The Johns Hopkins University, Baltimore, Md.

[21] Appl. No.: 08/370,235

[22] Filed: Jan. 9, 1995

Related U.S. Application Data

[63] Continuation of application No. 08/034,850, Mar. 19, 1993, abandoned.

[51] Int. Cl.$^6$ .................. G01N 33/574; G01N 33/53; G01N 33/572; G01N 33/537
[52] U.S. Cl. .................. 435/7.23; 435/7.9; 435/7.92; 436/64
[58] Field of Search .................. 530/387.7, 389.1, 530/389.8, 388.1, 809, 391.1; 435/7.23, 7.5, 7.9, 7.92, 21, 28; 436/540

[56] References Cited

FOREIGN PATENT DOCUMENTS 9213103 8/1992 WIPO.

OTHER PUBLICATIONS

Bulman, D.E, et al., *Genomics*, vol. 10, pp. 457–460, 1991.
Kinzler, K.W., et al, *Science*, vol. 253, pp. 661–665, Aug. 9, 1991.
*Antibodies; A Laboratory Manual*, Ed Harlow & David Lane, Cold Spring Harbor Publications, New York, pp. 72–76, 1988.
Varesco, et al., "CpG Island Clones From a Deletion Encompassing the Gene for Adenomatous Polyposis Coli," *Proc. Natl. Acad. Sci. USA* 86:10118–10122 (1989).
Hampton, et al., "Yeast Artificial Chromosomes for the Molecular Analysis of the Familial Polyposis APC Gene Region," *Proc. Natl. Acad. Sci. USA*, 89:8249–8253 (1992).
Miyoshi, et al., "Germ–line Mutations of the APC Gene in 53 Familial Adenomatous Polyposis Patients", *Proc. Natl. Acad. Sci., USA*, 89:4452–4456 (1992).
Miyoshi, et al., "Somatic Mutations in the APC Gene in Colorectal Tumors: Mutation Cluster Region in the APC Gene," *Human Molecular Genetics*, 1(4):229–233 (1992).
Powell, et al., "APC Mutations Occur Early During Colerectal Tumorigenesis," *Nature*, 359:235–237 (1992).
Laboratory Techniques in Biochemistry and Molecular Biology: Mononcal Antibody Technology, A.M. Campbell, Edited by R.H. Burden, Elsevier, Amsterdam, pp. 29–30, 1984.

International Search Report for PCT/US94/02987 dated Aug. 19, 1994.
Smith et al., "The APC Gene Product in Normal and Tumor Cells", *Proc. Natl. Acad. Sci. USA*, 90:2846–2850 (1993).
Nakatsuru et al., "Somatic Mutation of the APC Gene in Gastric Cancer: Frequent Mutations in Very Well Differentiated Adenocarcinoma and Signet–Ring Cell Carcinoma", *Human Molecular Genetics*, 1(8):559–563 (1992).
Nishisho et al., "Mutations of Chromosome 5q21 Genes in FAP and Colorectal Cancer Patients", *Science*, 253:665–669 (1991).
Bio–Rad catalog, pp. 194–194, 1990.
Sambrook et al, *Molecular Cloning:A laboratory manual*, Cold Spring Harbor Laboratory Press, 1989.
Sprague, K.U. "The Bombyx mori sild proteins: characterization of large polypeptides" Biochemistry, vol. 14, pp. 925–931, Abstract Only, 1975.
Kochevar, I.E. "UV–induced protein alterations and lipid oxidation in erythrocyte membranes" Photochem. Photobiol., vol. 52, pp. 795–800, Abstract Only, 1990.
Ugozzoli et al, "Separation and purification of high molecular weight glycoproteins using agarose gel electrophoresis" Biothechniques, vol. 12, pp. 187–188, Abstract Only, 1992.
Kimura et al, "Nereis cuticle collagen isolation and properties of a large fragment resistant to proteolysis by bacterial collagenase EC–3.4.4.19" J. Biol. Chem. vol. 252, pp. 8018–8022, Abstract Only, 1977.
Koch et al, "A Simple Immunoblotting Method after Separation of Proteins in Agarose Gel", The Journal of Immunological Methods, vol. 84, pp. 271–278, 1985.
Sprott et al, "Subcellular Fractionation of Murine Erythroleukemic Cells: Distribution of Protein Kinases", Analytical Biochemistry, vol. 194, pp. 407–412, 1991.
Roitt et al, *Immunology*, Chapter 9, pp. 9.2–9.7, Gower Medical Publishing, Ltd, 1985.
Kimball et al, *Introduction to Immunology*, Chapter 11, pp. 270–271, Macmillan Publishing Co., 1990.

*Primary Examiner*—Sheela Huff
*Assistant Examiner*—Yvonne Eyler
*Attorney, Agent, or Firm*—Banner & Witcoff, Ltd.

[57] ABSTRACT

Antibodies and assays employing them are taught which are useful for detecting the bulk of mutations which occur in the APC gene in familial adenomatous polyposis. The antibodies are specific for epitopes in the amino terminal or carboxy terminal portion of the protein. A variety of immunoassay formats are described which are all based on the observation that the bulk of the APC mutations which occur in familial adenomatous polyposis and sporadic colorectal carcinomas result in truncated APC proteins. Generally, either the size of APC proteins is determined or the relative binding of amino terminal-binding antibodies to carboxy terminal-binding antibodies is determined.

19 Claims, 4 Drawing Sheets

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 9606 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Homo sapiens (viii) POSITION IN GENOME:
      (B) MAP POSITION: 5q21

(ix) FEATURE:
      (A) NAME/KEY: CDS
      (B) LOCATION: 34..8562

(xi) SEQUENCE DESCRIPTION: SEQ ID NO:1:

```
GGACTCGGAA ATGAGGTCCA AGGGTAGCCA AGG ATG GCT GCA GCT TCA TAT GAT        54
                                    Met Ala Ala Ala Ser Tyr Asp
                                     1               5

CAG TTG TTA AAG CAA GTT GAG GCA CTG AAG ATG GAG AAC TCA AAT CTT        102
Gln Leu Leu Lys Gln Val Glu Ala Leu Lys Met Glu Asn Ser Asn Leu
             10                  15                  20

CGA CAA GAG CTA GAA GAT AAT TCC AAT CAT CTT ACA AAA CTG GAA ACT        150
Arg Gln Glu Leu Glu Asp Asn Ser Asn His Leu Thr Lys Leu Glu Thr
         25                  30                  35

GAG GCA TCT AAT ATG AAG GAA GTA CTT AAA CAA CTA CAA GGA AGT ATT        198
Glu Ala Ser Asn Met Lys Glu Val Leu Lys Gln Leu Gln Gly Ser Ile
 40              45                  50                  55

GAA GAT GAA GCT ATG GCT TCT TCT GGA CAG ATT GAT TTA TTA GAG CGT        246
Glu Asp Glu Ala Met Ala Ser Ser Gly Gln Ile Asp Leu Leu Glu Arg
                 60                  65                  70

CTT AAA GAG CTT AAC TTA GAT AGC AGT AAT TTC CCT GGA GTA AAA CTG        294
Leu Lys Glu Leu Asn Leu Asp Ser Ser Asn Phe Pro Gly Val Lys Leu
             75                  80                  85

CGG TCA AAA ATG TCC CTC CGT TCT TAT GGA AGC CGG GAA GGA TCT GTA        342
Arg Ser Lys Met Ser Leu Arg Ser Tyr Gly Ser Arg Glu Gly Ser Val
         90                  95                 100

TCA AGC CGT TCT GGA GAG TGC AGT CCT GTT CCT ATG GGT TCA TTT CCA        390
Ser Ser Arg Ser Gly Glu Cys Ser Pro Val Pro Met Gly Ser Phe Pro
        105                 110                 115

AGA AGA GGG TTT GTA AAT GGA AGC AGA GAA AGT ACT GGA TAT TTA GAA        438
Arg Arg Gly Phe Val Asn Gly Ser Arg Glu Ser Thr Gly Tyr Leu Glu
120                 125                 130                 135

GAA CTT GAG AAA GAG AGG TCA TTG CTT CTT GCT GAT CTT GAC AAA GAA        486
Glu Leu Glu Lys Glu Arg Ser Leu Leu Leu Ala Asp Leu Asp Lys Glu
                140                 145                 150
```

-continued

| | |
|---|---|
| GAA AAG GAA AAA GAC TGG TAT TAC GCT CAA CTT CAG AAT CTC ACT AAA<br>Glu Lys Glu Lys Asp Trp Tyr Tyr Ala Gln Leu Gln Asn Leu Thr Lys<br>155                            160                     165 | 534 |
| AGA ATA GAT AGT CTT CCT TTA ACT GAA AAT TTT TCC TTA CAA ACA GAT<br>Arg Ile Asp Ser Leu Pro Leu Thr Glu Asn Phe Ser Leu Gln Thr Asp<br>    170                          175                       180 | 582 |
| TTG ACC AGA AGG CAA TTG GAA TAT GAA GCA AGG CAA ATC AGA GTT GCG<br>Leu Thr Arg Arg Gln Leu Glu Tyr Glu Ala Arg Gln Ile Arg Val Ala<br>185                            190                     195 | 630 |
| ATG GAA GAA CAA CTA GGT ACC TGC CAG GAT ATG GAA AAA CGA GCA CAG<br>Met Glu Glu Gln Leu Gly Thr Cys Gln Asp Met Glu Lys Arg Ala Gln<br>200                            205                     210                     215 | 678 |
| CGA AGA ATA GCC AGA ATT CAG CAA ATC GAA AAG GAC ATA CTT CGT ATA<br>Arg Arg Ile Ala Arg Ile Gln Gln Ile Glu Lys Asp Ile Leu Arg Ile<br>                    220                          225                     230 | 726 |
| CGA CAG CTT TTA CAG TCC CAA GCA ACA GAA GCA GAG AGG TCA TCT CAG<br>Arg Gln Leu Leu Gln Ser Gln Ala Thr Glu Ala Glu Arg Ser Ser Gln<br>            235                          240                     245 | 774 |
| AAC AAG CAT GAA ACC GGC TCA CAT GAT GCT GAG CGG CAG AAT GAA GGT<br>Asn Lys His Glu Thr Gly Ser His Asp Ala Glu Arg Gln Asn Glu Gly<br>          250                          255                     260 | 822 |
| CAA GGA GTG GGA GAA ATC AAC ATG GCA ACT TCT GGT AAT GGT CAG GGT<br>Gln Gly Val Gly Glu Ile Asn Met Ala Thr Ser Gly Asn Gly Gln Gly<br>265                            270                     275 | 870 |
| TCA ACT ACA CGA ATG GAC CAT GAA ACA GCC AGT GTT TTG AGT TCT AGT<br>Ser Thr Thr Arg Met Asp His Glu Thr Ala Ser Val Leu Ser Ser Ser<br>280                            285                     290                     295 | 918 |
| AGC ACA CAC TCT GCA CCT CGA AGG CTG ACA AGT CAT CTG GGA ACC AAG<br>Ser Thr His Ser Ala Pro Arg Arg Leu Thr Ser His Leu Gly Thr Lys<br>                    300                          305                     310 | 966 |
| GTG GAA ATG GTG TAT TCA TTG TTG TCA ATG CTT GGT ACT CAT GAT AAG<br>Val Glu Met Val Tyr Ser Leu Leu Ser Met Leu Gly Thr His Asp Lys<br>                  315                          320                     325 | 1014 |
| GAT GAT ATG TCG CGA ACT TTG CTA GCT ATG TCT AGC TCC CAA GAC AGC<br>Asp Asp Met Ser Arg Thr Leu Leu Ala Met Ser Ser Ser Gln Asp Ser<br>330                            335                     340 | 1062 |
| TGT ATA TCC ATG CGA CAG TCT GGA TGT CTT CCT CTC CTC ATC CAG CTT<br>Cys Ile Ser Met Arg Gln Ser Gly Cys Leu Pro Leu Leu Ile Gln Leu<br>345                            350                     355 | 1110 |
| TTA CAT GGC AAT GAC AAA GAC TCT GTA TTG TTG GGA AAT TCC CGG GGC<br>Leu His Gly Asn Asp Lys Asp Ser Val Leu Leu Gly Asn Ser Arg Gly<br>360                            365                     370                     375 | 1158 |
| AGT AAA GAG GCT CGG GCC AGG GCC AGT GCA GCA CTC CAC AAC ATC ATT<br>Ser Lys Glu Ala Arg Ala Arg Ala Ser Ala Ala Leu His Asn Ile Ile<br>                  380                          385                     390 | 1206 |
| CAC TCA CAG CCT GAT GAC AAG AGA GGC AGG CGT GAA ATC CGA GTC CTT<br>His Ser Gln Pro Asp Asp Lys Arg Gly Arg Arg Glu Ile Arg Val Leu<br>                    395                          400                     405 | 1254 |
| CAT CTT TTG GAA CAG ATA CGC GCT TAC TGT GAA ACC TGT TGG GAG TGG<br>His Leu Leu Glu Gln Ile Arg Ala Tyr Cys Glu Thr Cys Trp Glu Trp<br>          410                          415                     420 | 1302 |
| CAG GAA GCT CAT GAA CCA GGC ATG GAC CAG GAC AAA AAT CCA ATG CCA<br>Gln Glu Ala His Glu Pro Gly Met Asp Gln Asp Lys Asn Pro Met Pro<br>425                            430                     435 | 1350 |
| GCT CCT GTT GAA CAT CAG ATC TGT CCT GCT GTG TGT GTT CTA ATG AAA<br>Ala Pro Val Glu His Gln Ile Cys Pro Ala Val Cys Val Leu Met Lys<br>440                            445                     450                     455 | 1398 |
| CTT TCA TTT GAT GAA GAG CAT AGA CAT GCA ATG AAT GAA CTA GGG GGA<br>Leu Ser Phe Asp Glu Glu His Arg His Ala Met Asn Glu Leu Gly Gly<br>                    460                          465                     470 | 1446 |

```
CTA CAG GCC ATT GCA GAA TTA TTG CAA GTG GAC TGT GAA ATG TAT GGG      1494
Leu Gln Ala Ile Ala Glu Leu Leu Gln Val Asp Cys Glu Met Tyr Gly
            475                 480                 485

CTT ACT AAT GAC CAC TAC AGT ATT ACA CTA AGA CGA TAT GCT GGA ATG      1542
Leu Thr Asn Asp His Tyr Ser Ile Thr Leu Arg Arg Tyr Ala Gly Met
        490                 495                 500

GCT TTG ACA AAC TTG ACT TTT GGA GAT GTA GCC AAC AAG GCT ACG CTA      1590
Ala Leu Thr Asn Leu Thr Phe Gly Asp Val Ala Asn Lys Ala Thr Leu
    505                 510                 515

TGC TCT ATG AAA GGC TGC ATG AGA GCA CTT GTG GCC CAA CTA AAA TCT      1638
Cys Ser Met Lys Gly Cys Met Arg Ala Leu Val Ala Gln Leu Lys Ser
520                 525                 530                 535

GAA AGT GAA GAC TTA CAG CAG GTT ATT GCA AGT GTT TTG AGG AAT TTG      1686
Glu Ser Glu Asp Leu Gln Gln Val Ile Ala Ser Val Leu Arg Asn Leu
                540                 545                 550

TCT TGG CGA GCA GAT GTA AAT AGT AAA AAG ACG TTG CGA GAA GTT GGA      1734
Ser Trp Arg Ala Asp Val Asn Ser Lys Lys Thr Leu Arg Glu Val Gly
            555                 560                 565

AGT GTG AAA GCA TTG ATG GAA TGT GCT TTA GAA GTT AAA AAG GAA TCA      1782
Ser Val Lys Ala Leu Met Glu Cys Ala Leu Glu Val Lys Lys Glu Ser
        570                 575                 580

ACC CTC AAA AGC GTA TTG AGT GCC TTA TGG AAT TTG TCA GCA CAT TGC      1830
Thr Leu Lys Ser Val Leu Ser Ala Leu Trp Asn Leu Ser Ala His Cys
    585                 590                 595

ACT GAG AAT AAA GCT GAT ATA TGT GCT GTA GAT GGT GCA CTT GCA TTT      1878
Thr Glu Asn Lys Ala Asp Ile Cys Ala Val Asp Gly Ala Leu Ala Phe
600                 605                 610                 615

TTG GTT GGC ACT CTT ACT TAC CGG AGC CAG ACA AAC ACT TTA GCC ATT      1926
Leu Val Gly Thr Leu Thr Tyr Arg Ser Gln Thr Asn Thr Leu Ala Ile
                620                 625                 630

ATT GAA AGT GGA GGT GGG ATA TTA CGG AAT GTG TCC AGC TTG ATA GCT      1974
Ile Glu Ser Gly Gly Gly Ile Leu Arg Asn Val Ser Ser Leu Ile Ala
            635                 640                 645

ACA AAT GAG GAC CAC AGG CAA ATC CTA AGA GAG AAC AAC TGT CTA CAA      2022
Thr Asn Glu Asp His Arg Gln Ile Leu Arg Glu Asn Asn Cys Leu Gln
        650                 655                 660

ACT TTA TTA CAA CAC TTA AAA TCT CAT AGT TTG ACA ATA GTC AGT AAT      2070
Thr Leu Leu Gln His Leu Lys Ser His Ser Leu Thr Ile Val Ser Asn
    665                 670                 675

GCA TGT GGA ACT TTG TGG AAT CTC TCA GCA AGA AAT CCT AAA GAC CAG      2118
Ala Cys Gly Thr Leu Trp Asn Leu Ser Ala Arg Asn Pro Lys Asp Gln
680                 685                 690                 695

GAA GCA TTA TGG GAC ATG GGG GCA GTT AGC ATG CTC AAG AAC CTC ATT      2166
Glu Ala Leu Trp Asp Met Gly Ala Val Ser Met Leu Lys Asn Leu Ile
                700                 705                 710

CAT TCA AAG CAC AAA ATG ATT GCT ATG GGA AGT GCT GCA GCT TTA AGG      2214
His Ser Lys His Lys Met Ile Ala Met Gly Ser Ala Ala Ala Leu Arg
            715                 720                 725

AAT CTC ATG GCA AAT AGG CCT GCG AAG TAC AAG GAT GCC AAT ATT ATG      2262
Asn Leu Met Ala Asn Arg Pro Ala Lys Tyr Lys Asp Ala Asn Ile Met
        730                 735                 740

TCT CCT GGC TCA AGC TTG CCA TCT CTT CAT GTT AGG AAA CAA AAA GCC      2310
Ser Pro Gly Ser Ser Leu Pro Ser Leu His Val Arg Lys Gln Lys Ala
    745                 750                 755

CTA GAA GCA GAA TTA GAT GCT CAG CAC TTA TCA GAA ACT TTT GAC AAT      2358
Leu Glu Ala Glu Leu Asp Ala Gln His Leu Ser Glu Thr Phe Asp Asn
760                 765                 770                 775

ATA GAC AAT TTA AGT CCC AAG GCA TCT CAT CGT AGT AAG CAG AGA CAC      2406
Ile Asp Asn Leu Ser Pro Lys Ala Ser His Arg Ser Lys Gln Arg His
                780                 785                 790
```

| | | |
|---|---|---|
| AAG CAA AGT CTC TAT GGT GAT TAT GTT TTT GAC ACC AAT CGA CAT GAT<br>Lys Gln Ser Leu Tyr Gly Asp Tyr Val Phe Asp Thr Asn Arg His Asp<br>795 800 805 | | 2454 |
| GAT AAT AGG TCA GAC AAT TTT AAT ACT GGC AAC ATG ACT GTC CTT TCA<br>Asp Asn Arg Ser Asp Asn Phe Asn Thr Gly Asn Met Thr Val Leu Ser<br>810 815 820 | | 2502 |
| CCA TAT TTG AAT ACT ACA GTG TTA CCC AGC TCC TCT TCA AGA GGA<br>Pro Tyr Leu Asn Thr Thr Val Leu Pro Ser Ser Ser Ser Arg Gly<br>825 830 835 | | 2550 |
| AGC TTA GAT AGT TCT CGT TCT GAA AAA GAT AGA AGT TTG GAG AGA GAA<br>Ser Leu Asp Ser Ser Arg Ser Glu Lys Asp Arg Ser Leu Glu Arg Glu<br>840 845 850 855 | | 2598 |
| CGC GGA ATT GGT CTA GGC AAC TAC CAT CCA GCA ACA GAA AAT CCA GGA<br>Arg Gly Ile Gly Leu Gly Asn Tyr His Pro Ala Thr Glu Asn Pro Gly<br>860 865 870 | | 2646 |
| ACT TCT TCA AAG CGA GGT TTG CAG ATC TCC ACC ACT GCA GCC CAG ATT<br>Thr Ser Ser Lys Arg Gly Leu Gln Ile Ser Thr Thr Ala Ala Gln Ile<br>875 880 885 | | 2694 |
| GCC AAA GTC ATG GAA GAA GTG TCA GCC ATT CAT ACC TCT CAG GAA GAC<br>Ala Lys Val Met Glu Glu Val Ser Ala Ile His Thr Ser Gln Glu Asp<br>890 895 900 | | 2742 |
| AGA AGT TCT GGG TCT ACC ACT GAA TTA CAT TGT GTG ACA GAT GAG AGA<br>Arg Ser Ser Gly Ser Thr Thr Glu Leu His Cys Val Thr Asp Glu Arg<br>905 910 915 | | 2790 |
| AAT GCA CTT AGA AGA AGC TCT GCT GCC CAT ACA CAT TCA AAC ACT TAC<br>Asn Ala Leu Arg Arg Ser Ser Ala Ala His Thr His Ser Asn Thr Tyr<br>920 925 930 935 | | 2838 |
| AAT TTC ACT AAG TCG GAA AAT TCA AAT AGG ACA TGT TCT ATG CCT TAT<br>Asn Phe Thr Lys Ser Glu Asn Ser Asn Arg Thr Cys Ser Met Pro Tyr<br>940 945 950 | | 2886 |
| GCC AAA TTA GAA TAC AAG AGA TCT TCA AAT GAT AGT TTA AAT AGT GTC<br>Ala Lys Leu Glu Tyr Lys Arg Ser Ser Asn Asp Ser Leu Asn Ser Val<br>955 960 965 | | 2934 |
| AGT AGT AAT GAT GGT TAT GGT AAA AGA GGT CAA ATG AAA CCC TCG ATT<br>Ser Ser Asn Asp Gly Tyr Gly Lys Arg Gly Gln Met Lys Pro Ser Ile<br>970 975 980 | | 2982 |
| GAA TCC TAT TCT GAA GAT GAT GAA AGT AAG TTT TGC AGT TAT GGT CAA<br>Glu Ser Tyr Ser Glu Asp Asp Glu Ser Lys Phe Cys Ser Tyr Gly Gln<br>985 990 995 | | 3030 |
| TAC CCA GCC GAC CTA GCC CAT AAA ATA CAT AGT GCA AAT CAT ATG GAT<br>Tyr Pro Ala Asp Leu Ala His Lys Ile His Ser Ala Asn His Met Asp<br>1000 1005 1010 1015 | | 3078 |
| GAT AAT GAT GGA GAA CTA GAT ACA CCA ATA AAT TAT AGT CTT AAA TAT<br>Asp Asn Asp Gly Glu Leu Asp Thr Pro Ile Asn Tyr Ser Leu Lys Tyr<br>1020 1025 1030 | | 3126 |
| TCA GAT GAG CAG TTG AAC TCT GGA AGG CAA AGT CCT TCA CAG AAT GAA<br>Ser Asp Glu Gln Leu Asn Ser Gly Arg Gln Ser Pro Ser Gln Asn Glu<br>1035 1040 1045 | | 3174 |
| AGA TGG GCA AGA CCC AAA CAC ATA ATA GAA GAT GAA ATA AAA CAA AGT<br>Arg Trp Ala Arg Pro Lys His Ile Ile Glu Asp Glu Ile Lys Gln Ser<br>1050 1055 1060 | | 3222 |
| GAG CAA AGA CAA TCA AGG AAT CAA AGT ACA ACT TAT CCT GTT TAT ACT<br>Glu Gln Arg Gln Ser Arg Asn Gln Ser Thr Thr Tyr Pro Val Tyr Thr<br>1065 1070 1075 | | 3270 |
| GAG AGC ACT GAT GAT AAA CAC CTC AAG TTC CAA CCA CAT TTT GGA CAG<br>Glu Ser Thr Asp Asp Lys His Leu Lys Phe Gln Pro His Phe Gly Gln<br>1080 1085 1090 1095 | | 3318 |
| CAG GAA TGT GTT TCT CCA TAC AGG TCA CGG GGA GCC AAT GGT TCA GAA<br>Gln Glu Cys Val Ser Pro Tyr Arg Ser Arg Gly Ala Asn Gly Ser Glu<br>1100 1105 1110 | | 3366 |

```
ACA AAT CGA GTG GGT TCT AAT CAT GGA ATT AAT CAA AAT GTA AGC CAG    3414
Thr Asn Arg Val Gly Ser Asn His Gly Ile Asn Gln Asn Val Ser Gln
            1115                1120                1125

TCT TTG TGT CAA GAA GAT GAC TAT GAA GAT GAT AAG CCT ACC AAT TAT    3462
Ser Leu Cys Gln Glu Asp Asp Tyr Glu Asp Asp Lys Pro Thr Asn Tyr
        1130                1135                1140

AGT GAA CGT TAC TCT GAA GAA GAA CAG CAT GAA GAA GAA GAG AGA CCA    3510
Ser Glu Arg Tyr Ser Glu Glu Glu Gln His Glu Glu Glu Glu Arg Pro
        1145                1150                1155

ACA AAT TAT AGC ATA AAA TAT AAT GAA GAG AAA CGT CAT GTG GAT CAG    3558
Thr Asn Tyr Ser Ile Lys Tyr Asn Glu Glu Lys Arg His Val Asp Gln
1160                1165                1170                1175

CCT ATT GAT TAT AGT TTA AAA TAT GCC ACA GAT ATT CCT TCA TCA CAG    3606
Pro Ile Asp Tyr Ser Leu Lys Tyr Ala Thr Asp Ile Pro Ser Ser Gln
                1180                1185                1190

AAA CAG TCA TTT TCA TTC TCA AAG AGT TCA TCT GGA CAA AGC AGT AAA    3654
Lys Gln Ser Phe Ser Phe Ser Lys Ser Ser Ser Gly Gln Ser Ser Lys
                    1195                1200                1205

ACC GAA CAT ATG TCT TCA AGC AGT GAG AAT ACG TCC ACA CCT TCA TCT    3702
Thr Glu His Met Ser Ser Ser Ser Glu Asn Thr Ser Thr Pro Ser Ser
                        1210                1215                1220

AAT GCC AAG AGG CAG AAT CAG CTC CAT CCA AGT TCT GCA CAG AGT AGA    3750
Asn Ala Lys Arg Gln Asn Gln Leu His Pro Ser Ser Ala Gln Ser Arg
        1225                1230                1235

AGT GGT CAG CCT CAA AAG GCT GCC ACT TGC AAA GTT TCT TCT ATT AAC    3798
Ser Gly Gln Pro Gln Lys Ala Ala Thr Cys Lys Val Ser Ser Ile Asn
1240                1245                1250                1255

CAA GAA ACA ATA CAG ACT TAT TGT GTA GAA GAT ACT CCA ATA TGT TTT    3846
Gln Glu Thr Ile Gln Thr Tyr Cys Val Glu Asp Thr Pro Ile Cys Phe
                1260                1265                1270

TCA AGA TGT AGT TCA TTA TCA TCT TTG TCA TCA GCT GAA GAT GAA ATA    3894
Ser Arg Cys Ser Ser Leu Ser Ser Leu Ser Ser Ala Glu Asp Glu Ile
            1275                1280                1285

GGA TGT AAT CAG ACG ACA CAG GAA GCA GAT TCT GCT AAT ACC CTG CAA    3942
Gly Cys Asn Gln Thr Thr Gln Glu Ala Asp Ser Ala Asn Thr Leu Gln
        1290                1295                1300

ATA GCA GAA ATA AAA GGA AAG ATT GGA ACT AGG TCA GCT GAA GAT CCT    3990
Ile Ala Glu Ile Lys Gly Lys Ile Gly Thr Arg Ser Ala Glu Asp Pro
    1305                1310                1315

GTG AGC GAA GTT CCA GCA GTG TCA CAG CAC CCT AGA ACC AAA TCC AGC    4038
Val Ser Glu Val Pro Ala Val Ser Gln His Pro Arg Thr Lys Ser Ser
1320                1325                1330                1335

AGA CTG CAG GGT TCT AGT TTA TCT TCA GAA TCA GCC AGG CAC AAA GCT    4086
Arg Leu Gln Gly Ser Ser Leu Ser Ser Glu Ser Ala Arg His Lys Ala
                1340                1345                1350

GTT GAA TTT CCT TCA GGA GCG AAA TCT CCC TCC AAA AGT GGT GCT CAG    4134
Val Glu Phe Pro Ser Gly Ala Lys Ser Pro Ser Lys Ser Gly Ala Gln
            1355                1360                1365

ACA CCC AAA AGT CCA CCT GAA CAC TAT GTT CAG GAG ACC CCA CTC ATG    4182
Thr Pro Lys Ser Pro Pro Glu His Tyr Val Gln Glu Thr Pro Leu Met
        1370                1375                1380

TTT AGC AGA TGT ACT TCT GTC AGT TCA CTT GAT AGT TTT GAG AGT CGT    4230
Phe Ser Arg Cys Thr Ser Val Ser Ser Leu Asp Ser Phe Glu Ser Arg
    1385                1390                1395

TCG ATT GCC AGC TCC GTT CAG AGT GAA CCA TGC AGT GGA ATG GTA AGT    4278
Ser Ile Ala Ser Ser Val Gln Ser Glu Pro Cys Ser Gly Met Val Ser
1400                1405                1410                1415

GGC ATT ATA AGC CCC AGT GAT CTT CCA GAT AGC CCT GGA CAA ACC ATG    4326
Gly Ile Ile Ser Pro Ser Asp Leu Pro Asp Ser Pro Gly Gln Thr Met
                1420                1425                1430
```

-continued

| | | | | | | | | | | | | | | | |
|---|---|---|---|---|---|---|---|---|---|---|---|---|---|---|---|
| CCA | CCA | AGC | AGA | AGT | AAA | ACA | CCT | CCA | CCA | CCT | CCT | CAA | ACA | GCT | CAA | 4374 |
| Pro | Pro | Ser | Arg | Ser | Lys | Thr | Pro | Pro | Pro | Pro | Pro | Gln | Thr | Ala | Gln | |
| | | | 1435 | | | | 1440 | | | | | 1445 | | | | |

```
CCA CCA AGC AGA AGT AAA ACA CCT CCA CCA CCT CCT CAA ACA GCT CAA    4374
Pro Pro Ser Arg Ser Lys Thr Pro Pro Pro Pro Pro Gln Thr Ala Gln
            1435            1440                1445

ACC AAG CGA GAA GTA CCT AAA AAT AAA GCA CCT ACT GCT GAA AAG AGA    4422
Thr Lys Arg Glu Val Pro Lys Asn Lys Ala Pro Thr Ala Glu Lys Arg
        1450            1455            1460

GAG AGT GGA CCT AAG CAA GCT GCA GTA AAT GCT GCA GTT CAG AGG GTC    4470
Glu Ser Gly Pro Lys Gln Ala Ala Val Asn Ala Ala Val Gln Arg Val
        1465            1470            1475

CAG GTT CTT CCA GAT GCT GAT ACT TTA TTA CAT TTT GCC ACA GAA AGT    4518
Gln Val Leu Pro Asp Ala Asp Thr Leu Leu His Phe Ala Thr Glu Ser
1480            1485            1490                1495

ACT CCA GAT GGA TTT TCT TGT TCA TCC AGC CTG AGT GCT CTG AGC CTC    4566
Thr Pro Asp Gly Phe Ser Cys Ser Ser Ser Leu Ser Ala Leu Ser Leu
                1500            1505            1510

GAT GAG CCA TTT ATA CAG AAA GAT GTG GAA TTA AGA ATA ATG CCT CCA    4614
Asp Glu Pro Phe Ile Gln Lys Asp Val Glu Leu Arg Ile Met Pro Pro
            1515            1520            1525

GTT CAG GAA AAT GAC AAT GGG AAT GAA ACA GAA TCA GAG CAG CCT AAA    4662
Val Gln Glu Asn Asp Asn Gly Asn Glu Thr Glu Ser Glu Gln Pro Lys
        1530            1535            1540

GAA TCA AAT GAA AAC CAA GAG AAA GAG GCA GAA AAA ACT ATT GAT TCT    4710
Glu Ser Asn Glu Asn Gln Glu Lys Glu Ala Glu Lys Thr Ile Asp Ser
        1545            1550            1555

GAA AAG GAC CTA TTA GAT GAT TCA GAT GAT GAT GAT ATT GAA ATA CTA    4758
Glu Lys Asp Leu Leu Asp Asp Ser Asp Asp Asp Asp Ile Glu Ile Leu
1560            1565            1570                1575

GAA GAA TGT ATT ATT TCT GCC ATG CCA ACA AAG TCA TCA CGT AAA GGC    4806
Glu Glu Cys Ile Ile Ser Ala Met Pro Thr Lys Ser Ser Arg Lys Gly
                1580            1585            1590

AAA AAG CCA GCC CAG ACT GCT TCA AAA TTA CCT CCA CCT GTG GCA AGG    4854
Lys Lys Pro Ala Gln Thr Ala Ser Lys Leu Pro Pro Pro Val Ala Arg
            1595            1600            1605

AAA CCA AGT CAG CTG CCT GTG TAC AAA CTT CTA CCA TCA CAA AAC AGG    4902
Lys Pro Ser Gln Leu Pro Val Tyr Lys Leu Leu Pro Ser Gln Asn Arg
            1610            1615            1620

TTG CAA CCC CAA AAG CAT GTT AGT TTT ACA CCG GGG GAT GAT ATG CCA    4950
Leu Gln Pro Gln Lys His Val Ser Phe Thr Pro Gly Asp Asp Met Pro
            1625            1630            1635

CGG GTG TAT TGT GTT GAA GGG ACA CCT ATA AAC TTT TCC ACA GCT ACA    4998
Arg Val Tyr Cys Val Glu Gly Thr Pro Ile Asn Phe Ser Thr Ala Thr
1640            1645            1650            1655

TCT CTA AGT GAT CTA ACA ATC GAA TCC CCT CCA AAT GAG TTA GCT GCT    5046
Ser Leu Ser Asp Leu Thr Ile Glu Ser Pro Pro Asn Glu Leu Ala Ala
                1660            1665            1670

GGA GAA GGA GTT AGA GGA GGA GCA CAG TCA GGT GAA TTT GAA AAA CGA    5094
Gly Glu Gly Val Arg Gly Gly Ala Gln Ser Gly Glu Phe Glu Lys Arg
            1675            1680            1685

GAT ACC ATT CCT ACA GAA GGC AGA AGT ACA GAT GAG GCT CAA GGA GGA    5142
Asp Thr Ile Pro Thr Glu Gly Arg Ser Thr Asp Glu Ala Gln Gly Gly
            1690            1695            1700

AAA ACC TCA TCT GTA ACC ATA CCT GAA TTG GAT GAC AAT AAA GCA GAG    5190
Lys Thr Ser Ser Val Thr Ile Pro Glu Leu Asp Asp Asn Lys Ala Glu
        1705            1710            1715

GAA GGT GAT ATT CTT GCA GAA TGC ATT AAT TCT GCT ATG CCC AAA GGG    5238
Glu Gly Asp Ile Leu Ala Glu Cys Ile Asn Ser Ala Met Pro Lys Gly
        1720            1725            1730            1735

AAA AGT CAC AAG CCT TTC CGT GTG AAA AAG ATA ATG GAC CAG GTC CAG    5286
Lys Ser His Lys Pro Phe Arg Val Lys Lys Ile Met Asp Gln Val Gln
            1740            1745            1750
```

```
CAA GCA TCT GCG TCG TCT TCT GCA CCC AAC AAA AAT CAG TTA GAT GGT    5334
Gln Ala Ser Ala Ser Ser Ser Ala Pro Asn Lys Asn Gln Leu Asp Gly
        1755                1760                1765

AAG AAA AAG AAA CCA ACT TCA CCA GTA AAA CCT ATA CCA CAA AAT ACT    5382
Lys Lys Lys Lys Pro Thr Ser Pro Val Lys Pro Ile Pro Gln Asn Thr
    1770                1775                1780

GAA TAT AGG ACA CGT GTA AGA AAA AAT GCA GAC TCA AAA AAT AAT TTA    5430
Glu Tyr Arg Thr Arg Val Arg Lys Asn Ala Asp Ser Lys Asn Asn Leu
    1785                1790                1795

AAT GCT GAG AGA GTT TTC TCA GAC AAC AAA GAT TCA AAG AAA CAG AAT    5478
Asn Ala Glu Arg Val Phe Ser Asp Asn Lys Asp Ser Lys Lys Gln Asn
1800                1805                1810                1815

TTG AAA AAT AAT TCC AAG GAC TTC AAT GAT AAG CTC CCA AAT AAT GAA    5526
Leu Lys Asn Asn Ser Lys Asp Phe Asn Asp Lys Leu Pro Asn Asn Glu
        1820                1825                1830

GAT AGA GTC AGA GGA AGT TTT GCT TTT GAT TCA CCT CAT CAT TAC ACG    5574
Asp Arg Val Arg Gly Ser Phe Ala Phe Asp Ser Pro His His Tyr Thr
    1835                1840                1845

CCT ATT GAA GGA ACT CCT TAC TGT TTT TCA CGA AAT GAT TCT TTG AGT    5622
Pro Ile Glu Gly Thr Pro Tyr Cys Phe Ser Arg Asn Asp Ser Leu Ser
    1850                1855                1860

TCT CTA GAT TTT GAT GAT GAT GAT GTT GAC CTT TCC AGG GAA AAG GCT    5670
Ser Leu Asp Phe Asp Asp Asp Asp Val Asp Leu Ser Arg Glu Lys Ala
    1865                1870                1875

GAA TTA AGA AAG GCA AAA GAA AAT AAG GAA TCA GAG GCT AAA GTT ACC    5718
Glu Leu Arg Lys Ala Lys Glu Asn Lys Glu Ser Glu Ala Lys Val Thr
1880                1885                1890                1895

AGC CAC ACA GAA CTA ACC TCC AAC CAA CAA TCA GCT AAT AAG ACA CAA    5766
Ser His Thr Glu Leu Thr Ser Asn Gln Gln Ser Ala Asn Lys Thr Gln
        1900                1905                1910

GCT ATT GCA AAG CAG CCA ATA AAT CGA GGT CAG CCT AAA CCC ATA CTT    5814
Ala Ile Ala Lys Gln Pro Ile Asn Arg Gly Gln Pro Lys Pro Ile Leu
    1915                1920                1925

CAG AAA CAA TCC ACT TTT CCC CAG TCA TCC AAA GAC ATA CCA GAC AGA    5862
Gln Lys Gln Ser Thr Phe Pro Gln Ser Ser Lys Asp Ile Pro Asp Arg
    1930                1935                1940

GGG GCA GCA ACT GAT GAA AAG TTA CAG AAT TTT GCT ATT GAA AAT ACT    5910
Gly Ala Ala Thr Asp Glu Lys Leu Gln Asn Phe Ala Ile Glu Asn Thr
    1945                1950                1955

CCA GTT TGC TTT TCT CAT AAT TCC TCT CTG AGT TCT CTC AGT GAC ATT    5958
Pro Val Cys Phe Ser His Asn Ser Ser Leu Ser Ser Leu Ser Asp Ile
1960                1965                1970                1975

GAC CAA GAA AAC AAC AAT AAA GAA AAT GAA CCT ATC AAA GAG ACT GAG    6006
Asp Gln Glu Asn Asn Asn Lys Glu Asn Glu Pro Ile Lys Glu Thr Glu
        1980                1985                1990

CCC CCT GAC TCA CAG GGA GAA CCA AGT AAA CCT CAA GCA TCA GGC TAT    6054
Pro Pro Asp Ser Gln Gly Glu Pro Ser Lys Pro Gln Ala Ser Gly Tyr
    1995                2000                2005

GCT CCT AAA TCA TTT CAT GTT GAA GAT ACC CCA GTT TGT TTC TCA AGA    6102
Ala Pro Lys Ser Phe His Val Glu Asp Thr Pro Val Cys Phe Ser Arg
    2010                2015                2020

AAC AGT TCT CTC AGT TCT CTT AGT ATT GAC TCT GAA GAT GAC CTG TTG    6150
Asn Ser Ser Leu Ser Ser Leu Ser Ile Asp Ser Glu Asp Asp Leu Leu
2025                2030                2035

CAG GAA TGT ATA AGC TCC GCA ATG CCA AAA AAG AAA AAG CCT TCA AGA    6198
Gln Glu Cys Ile Ser Ser Ala Met Pro Lys Lys Lys Lys Pro Ser Arg
2040                2045                2050                2055

CTC AAG GGT GAT AAT GAA AAA CAT AGT CCC AGA AAT ATG GGT GGC ATA    6246
Leu Lys Gly Asp Asn Glu Lys His Ser Pro Arg Asn Met Gly Gly Ile
        2060                2065                2070
```

```
TTA GGT GAA GAT CTG ACA CTT GAT TTG AAA GAT ATA CAG AGA CCA GAT      6294
Leu Gly Glu Asp Leu Thr Leu Asp Leu Lys Asp Ile Gln Arg Pro Asp
        2075                2080                2085

TCA GAA CAT GGT CTA TCC CCT GAT TCA GAA AAT TTT GAT TGG AAA GCT      6342
Ser Glu His Gly Leu Ser Pro Asp Ser Glu Asn Phe Asp Trp Lys Ala
        2090                2095                2100

ATT CAG GAA GGT GCA AAT TCC ATA GTA AGT AGT TTA CAT CAA GCT GCT      6390
Ile Gln Glu Gly Ala Asn Ser Ile Val Ser Ser Leu His Gln Ala Ala
        2105                2110                2115

GCT GCT GCA TGT TTA TCT AGA CAA GCT TCG TCT GAT TCA GAT TCC ATC      6438
Ala Ala Ala Cys Leu Ser Arg Gln Ala Ser Ser Asp Ser Asp Ser Ile
2120            2125                2130                2135

CTT TCC CTG AAA TCA GGA ATC TCT CTG GGA TCA CCA TTT CAT CTT ACA      6486
Leu Ser Leu Lys Ser Gly Ile Ser Leu Gly Ser Pro Phe His Leu Thr
                2140                2145                2150

CCT GAT CAA GAA GAA AAA CCC TTT ACA AGT AAT AAA GGC CCA CGA ATT      6534
Pro Asp Gln Glu Glu Lys Pro Phe Thr Ser Asn Lys Gly Pro Arg Ile
            2155                2160                2165

CTA AAA CCA GGG GAG AAA AGT ACA TTG GAA ACT AAA AAG ATA GAA TCT      6582
Leu Lys Pro Gly Glu Lys Ser Thr Leu Glu Thr Lys Lys Ile Glu Ser
        2170                2175                2180

GAA AGT AAA GGA ATC AAA GGA GGA AAA AAA GTT TAT AAA AGT TTG ATT      6630
Glu Ser Lys Gly Ile Lys Gly Gly Lys Lys Val Tyr Lys Ser Leu Ile
        2185                2190                2195

ACT GGA AAA GTT CGA TCT AAT TCA GAA ATT TCA GGC CAA ATG AAA CAG      6678
Thr Gly Lys Val Arg Ser Asn Ser Glu Ile Ser Gly Gln Met Lys Gln
2200            2205                2210                2215

CCC CTT CAA GCA AAC ATG CCT TCA ATC TCT CGA GGC AGG ACA ATG ATT      6726
Pro Leu Gln Ala Asn Met Pro Ser Ile Ser Arg Gly Arg Thr Met Ile
                2220                2225                2230

CAT ATT CCA GGA GTT CGA AAT AGC TCC TCA AGT ACA AGT CCT GTT TCT      6774
His Ile Pro Gly Val Arg Asn Ser Ser Ser Ser Thr Ser Pro Val Ser
            2235                2240                2245

AAA AAA GGC CCA CCC CTT AAG ACT CCA GCC TCC AAA AGC CCT AGT GAA      6822
Lys Lys Gly Pro Pro Leu Lys Thr Pro Ala Ser Lys Ser Pro Ser Glu
        2250                2255                2260

GGT CAA ACA GCC ACC ACT TCT CCT AGA GGA GCC AAG CCA TCT GTG AAA      6870
Gly Gln Thr Ala Thr Thr Ser Pro Arg Gly Ala Lys Pro Ser Val Lys
        2265                2270                2275

TCA GAA TTA AGC CCT GTT GCC AGG CAG ACA TCC CAA ATA GGT GGG TCA      6918
Ser Glu Leu Ser Pro Val Ala Arg Gln Thr Ser Gln Ile Gly Gly Ser
2280            2285                2290                2295

AGT AAA GCA CCT TCT AGA TCA GGA TCT AGA GAT TCG ACC CCT TCA AGA      6966
Ser Lys Ala Pro Ser Arg Ser Gly Ser Arg Asp Ser Thr Pro Ser Arg
                2300                2305                2310

CCT GCC CAG CAA CCA TTA AGT AGA CCT ATA CAG TCT CCT GGC CGA AAC      7014
Pro Ala Gln Gln Pro Leu Ser Arg Pro Ile Gln Ser Pro Gly Arg Asn
            2315                2320                2325

TCA ATT TCC CCT GGT AGA AAT GGA ATA AGT CCT CCT AAC AAA TTA TCT      7062
Ser Ile Ser Pro Gly Arg Asn Gly Ile Ser Pro Pro Asn Lys Leu Ser
        2330                2335                2340

CAA CTT CCA AGG ACA TCA TCC CCT AGT ACT GCT TCA ACT AAG TCC TCA      7110
Gln Leu Pro Arg Thr Ser Ser Pro Ser Thr Ala Ser Thr Lys Ser Ser
        2345                2350                2355

GGT TCT GGA AAA ATG TCA TAT ACA TCT CCA GGT AGA CAG ATG AGC CAA      7158
Gly Ser Gly Lys Met Ser Tyr Thr Ser Pro Gly Arg Gln Met Ser Gln
2360            2365                2370                2375

CAG AAC CTT ACC AAA CAA ACA GGT TTA TCC AAG AAT GCC AGT AGT ATT      7206
Gln Asn Leu Thr Lys Gln Thr Gly Leu Ser Lys Asn Ala Ser Ser Ile
                2380                2385                2390
```

| | |
|---|---|
| CCA AGA AGT GAG TCT GCC TCC AAA GGA CTA AAT CAG ATG AAT AAT GGT<br>Pro Arg Ser Glu Ser Ala Ser Lys Gly Leu Asn Gln Met Asn Asn Gly<br>2395                              2400                            2405 | 7254 |
| AAT GGA GCC AAT AAA AAG GTA GAA CTT TCT AGA ATG TCT TCA ACT AAA<br>Asn Gly Ala Asn Lys Lys Val Glu Leu Ser Arg Met Ser Ser Thr Lys<br>2410                              2415                            2420 | 7302 |
| TCA AGT GGA AGT GAA TCT GAT AGA TCA GAA AGA CCT GTA TTA GTA CGC<br>Ser Ser Gly Ser Glu Ser Asp Arg Ser Glu Arg Pro Val Leu Val Arg<br>2425                              2430                            2435 | 7350 |
| CAG TCA ACT TTC ATC AAA GAA GCT CCA AGC CCA ACC TTA AGA AGA AAA<br>Gln Ser Thr Phe Ile Lys Glu Ala Pro Ser Pro Thr Leu Arg Arg Lys<br>2440                              2445                            2455 | 7398 |
| TTG GAG GAA TCT GCT TCA TTT GAA TCT CTT TCT CCA TCA TCT AGA CCA<br>Leu Glu Glu Ser Ala Ser Phe Glu Ser Leu Ser Pro Ser Ser Arg Pro<br>                      2460                            2465                            2470 | 7446 |
| GCT TCT CCC ACT AGG TCC CAG GCA CAA ACT CCA GTT TTA AGT CCT TCC<br>Ala Ser Pro Thr Arg Ser Gln Ala Gln Thr Pro Val Leu Ser Pro Ser<br>                      2475                            2480                            2485 | 7494 |
| CTT CCT GAT ATG TCT CTA TCC ACA CAT TCG TCT GTT CAG GCT GGT GGA<br>Leu Pro Asp Met Ser Leu Ser Thr His Ser Ser Val Gln Ala Gly Gly<br>                      2490                            2495                            2500 | 7542 |
| TGG CGA AAA CTC CCA CCT AAT CTC AGT CCC ACT ATA GAG TAT AAT GAT<br>Trp Arg Lys Leu Pro Pro Asn Leu Ser Pro Thr Ile Glu Tyr Asn Asp<br>                      2505                            2510                            2515 | 7590 |
| GGA AGA CCA GCA AAG CGC CAT GAT ATT GCA CGG TCT CAT TCT GAA AGT<br>Gly Arg Pro Ala Lys Arg His Asp Ile Ala Arg Ser His Ser Glu Ser<br>2520                              2525                            2530                            2535 | 7638 |
| CCT TCT AGA CTT CCA ATC AAT AGG TCA GGA ACC TGG AAA CGT GAG CAC<br>Pro Ser Arg Leu Pro Ile Asn Arg Ser Gly Thr Trp Lys Arg Glu His<br>                      2540                            2545                            2550 | 7686 |
| AGC AAA CAT TCA TCA TCC CTT CCT CGA GTA AGC ACT TGG AGA AGA ACT<br>Ser Lys His Ser Ser Ser Leu Pro Arg Val Ser Thr Trp Arg Arg Thr<br>                      2555                            2560                            2565 | 7734 |
| GGA AGT TCA TCT TCA ATT CTT TCT GCT TCA TCA GAA TCC AGT GAA AAA<br>Gly Ser Ser Ser Ser Ile Leu Ser Ala Ser Ser Glu Ser Ser Glu Lys<br>                      2570                            2575                            2580 | 7782 |
| GCA AAA AGT GAG GAT GAA AAA CAT GTG AAC TCT ATT TCA GGA ACC AAA<br>Ala Lys Ser Glu Asp Glu Lys His Val Asn Ser Ile Ser Gly Thr Lys<br>2585                              2590                            2595 | 7830 |
| CAA AGT AAA GAA AAC CAA GTA TCC GCA AAA GGA ACA TGG AGA AAA ATA<br>Gln Ser Lys Glu Asn Gln Val Ser Ala Lys Gly Thr Trp Arg Lys Ile<br>2600                              2605                            2610                            2615 | 7878 |
| AAA GAA AAT GAA TTT TCT CCC ACA AAT AGT ACT TCT CAG ACC GTT TCC<br>Lys Glu Asn Glu Phe Ser Pro Thr Asn Ser Thr Ser Gln Thr Val Ser<br>                      2620                            2625                            2630 | 7926 |
| TCA GGT GCT ACA AAT GGT GCT GAA TCA AAG ACT CTA ATT TAT CAA ATG<br>Ser Gly Ala Thr Asn Gly Ala Glu Ser Lys Thr Leu Ile Tyr Gln Met<br>                      2635                            2640                            2645 | 7974 |
| GCA CCT GCT GTT TCT AAA ACA GAG GAT GTT TGG GTG AGA ATT GAG GAC<br>Ala Pro Ala Val Ser Lys Thr Glu Asp Val Trp Val Arg Ile Glu Asp<br>                      2650                            2655                            2660 | 8022 |
| TGT CCC ATT AAC AAT CCT AGA TCT GGA AGA TCT CCC ACA GGT AAT ACT<br>Cys Pro Ile Asn Asn Pro Arg Ser Gly Arg Ser Pro Thr Gly Asn Thr<br>                      2665                            2670                            2675 | 8070 |
| CCC CCG GTG ATT GAC AGT GTT TCA GAA AAG GCA AAT CCA AAC ATT AAA<br>Pro Pro Val Ile Asp Ser Val Ser Glu Lys Ala Asn Pro Asn Ile Lys<br>2680                              2685                            2690                            2695 | 8118 |
| GAT TCA AAA GAT AAT CAG GCA AAA CAA AAT GTG GGT AAT GGC AGT GTT<br>Asp Ser Lys Asp Asn Gln Ala Lys Gln Asn Val Gly Asn Gly Ser Val<br>                      2700                            2705                            2710 | 8166 |

33
—continued

| | | |
|---|---|---|
| CCC ATG CGT ACC GTG GGT TTG GAA AAT CGC CTG ACC TCC TTT ATT CAG<br>Pro Met Arg Thr Val Gly Leu Glu Asn Arg Leu Thr Ser Phe Ile Gln<br>2715                         2720                     2725 | | 8214 |
| GTG GAT GCC CCT GAC CAA AAA GGA ACT GAG ATA AAA CCA GGA CAA AAT<br>Val Asp Ala Pro Asp Gln Lys Gly Thr Glu Ile Lys Pro Gly Gln Asn<br>2730                        2735                     2740 | | 8262 |
| AAT CCT GTC CCT GTA TCA GAG ACT AAT GAA AGT CCT ATA GTG GAA CGT<br>Asn Pro Val Pro Val Ser Glu Thr Asn Glu Ser Pro Ile Val Glu Arg<br>2745                        2750                     2755 | | 8310 |
| ACC CCA TTC AGT TCT AGC AGC TCA AGC AAA CAC AGT TCA CCT AGT GGG<br>Thr Pro Phe Ser Ser Ser Ser Ser Ser Lys His Ser Ser Pro Ser Gly<br>2760                        2765                     2770                     2775 | | 8358 |
| ACT GTT GCT GCC AGA GTG ACT CCT TTT AAT TAC AAC CCA AGC CCT AGG<br>Thr Val Ala Ala Arg Val Thr Pro Phe Asn Tyr Asn Pro Ser Pro Arg<br>                     2780                     2785                     2790 | | 8406 |
| AAA AGC AGC GCA GAT AGC ACT TCA GCT CGG CCA TCT CAG ATC CCA ACT<br>Lys Ser Ser Ala Asp Ser Thr Ser Ala Arg Pro Ser Gln Ile Pro Thr<br>                     2795                     2800                     2805 | | 8454 |
| CCA GTG AAT AAC AAC ACA AAG AAG CGA GAT TCC AAA ACT GAC AGC ACA<br>Pro Val Asn Asn Asn Thr Lys Lys Arg Asp Ser Lys Thr Asp Ser Thr<br>          2810                     2815                     2820 | | 8502 |
| GAA TCC AGT GGA ACC CAA AGT CCT AAG CGC CAT TCT GGG TCT TAC CTT<br>Glu Ser Ser Gly Thr Gln Ser Pro Lys Arg His Ser Gly Ser Tyr Leu<br>2825                        2830                     2835 | | 8550 |
| GTG ACA TCT GTT TAAAAGAGAG GAAGAATGAA ACTAAGAAAA TTCTATGTTA<br>Val Thr Ser Val<br>2840 | | 8602 |
| ATTACAACTG CTATATAGAC ATTTTGTTTC AAATGAAACT TTAAAAGACT GAAAATTTT | | 8662 |
| GTAAATAGGT TGATTCTTG TTAGAGGGTT TTTGTTCTGG AAGCCATATT TGATAGTATA | | 8722 |
| CTTTGTCTTC ACTGGTCTTA TTTTGGGAGG CACTCTTGAT GGTTAGGAAA AAATAGAAAG | | 8782 |
| CCAAGTATGT TTGTACAGTA TGTTTTACAT GTATTTAAAG TAGCATCCCA TCCCAACTTC | | 8842 |
| CTTAATTATT GCTTGTCTAA AATAATGAAC ACTACAGATA GGAAATATGA TATATTGCTG | | 8902 |
| TTATCAATCA TTTCTAGATT ATAAACTGAC TAAACTTACA TCAGGGGAAA ATTGGTATTT | | 8962 |
| ATGCAAAAAA AAAATGTTTT TGTCCTTGTG AGTCCATCTA ACATCATAAT TAATCATGTG | | 9022 |
| GCTGTGAAAT TCACAGTAAT ATGGTTCCCG ATGAACAAGT TTACCCAGCC TGCTTTGCTT | | 9082 |
| ACTGCATGAA TGAAACTGAT GGTTCAATTT CAGAAGTAAT GATTAACAGT TATGTGGTCA | | 9142 |
| CATGATGTGC ATAGAGATAG CTACAGTGTA ATAATTTACA CTATTTTGTG CTCCAAACAA | | 9202 |
| AACAAAAATC TGTGTAACTG TAAAACATTG AATGAAACTA TTTTACCTGA ACTAGATTTT | | 9262 |
| ATCTGAAAGT AGGTAGAATT TTTGCTATGC TGTAATTTGT TGTATATTCT GGTATTTGAG | | 9322 |
| GTGAGATGGC TGCTCTTTAT TAATGAGACA TGAATTGTGT CTCAACAGAA ACTAAATGAA | | 9382 |
| CATTTCAGAA TAAATTATTG CTGTATGTAA ACTGTTACTG AAATTGGTAT TTGTTTGAAG | | 9442 |
| GGTTTGTTTC ACATTTGTAT TAATTAATTG TTTAAAATGC CTCTTTTAAA AGCTTATATA | | 9502 |
| AATTTTTTCT TCAGCTTCTA TGCATTAAGA GTAAAATTCC TCTTACTGTA ATAAAAACAT | | 9562 |
| TGAAGAAGAC TGTTGCCACT TAACCATTCC ATGCGTTGGC ACTT | | 9606 |

(2) INFORMATION FOR SEQ ID NO:2:

(i) SEQUENCE CHARACTERISTICS:
        (A) LENGTH: 2843 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Ala Ser Tyr Asp Gln Leu Leu Lys Gln Val Glu Ala Leu
 1               5                  10                  15

Lys Met Glu Asn Ser Asn Leu Arg Gln Glu Leu Glu Asp Asn Ser Asn
            20                  25                  30

His Leu Thr Lys Leu Glu Thr Glu Ala Ser Asn Met Lys Glu Val Leu
                35                  40                  45

Lys Gln Leu Gln Gly Ser Ile Glu Asp Glu Ala Met Ala Ser Ser Gly
     50                  55                  60

Gln Ile Asp Leu Leu Glu Arg Leu Lys Glu Leu Asn Leu Asp Ser Ser
 65                  70                  75                  80

Asn Phe Pro Gly Val Lys Leu Arg Ser Lys Met Ser Leu Arg Ser Tyr
                85                  90                  95

Gly Ser Arg Glu Gly Ser Val Ser Ser Arg Ser Gly Glu Cys Ser Pro
                100                 105                 110

Val Pro Met Gly Ser Phe Pro Arg Arg Gly Phe Val Asn Gly Ser Arg
            115                 120                 125

Glu Ser Thr Gly Tyr Leu Glu Glu Leu Glu Lys Glu Arg Ser Leu Leu
            130                 135                 140

Leu Ala Asp Leu Asp Lys Glu Glu Lys Glu Lys Asp Trp Tyr Tyr Ala
145                 150                 155                 160

Gln Leu Gln Asn Leu Thr Lys Arg Ile Asp Ser Leu Pro Leu Thr Glu
                165                 170                 175

Asn Phe Ser Leu Gln Thr Asp Leu Thr Arg Arg Gln Leu Glu Tyr Glu
            180                 185                 190

Ala Arg Gln Ile Arg Val Ala Met Glu Glu Gln Leu Gly Thr Cys Gln
        195                 200                 205

Asp Met Glu Lys Arg Ala Gln Arg Arg Ile Ala Arg Ile Gln Gln Ile
210                 215                 220

Glu Lys Asp Ile Leu Arg Ile Arg Gln Leu Leu Gln Ser Gln Ala Thr
225                 230                 235                 240

Glu Ala Glu Arg Ser Ser Gln Asn Lys His Glu Thr Gly Ser His Asp
                245                 250                 255

Ala Glu Arg Gln Asn Glu Gly Gln Gly Val Gly Glu Ile Asn Met Ala
            260                 265                 270

Thr Ser Gly Asn Gly Gln Gly Ser Thr Thr Arg Met Asp His Glu Thr
            275                 280                 285

Ala Ser Val Leu Ser Ser Ser Thr His Ser Ala Pro Arg Arg Leu
290                 295                 300

Thr Ser His Leu Gly Thr Lys Val Glu Met Val Tyr Ser Leu Leu Ser
305                 310                 315                 320

Met Leu Gly Thr His Asp Lys Asp Asp Met Ser Arg Thr Leu Leu Ala
                325                 330                 335

Met Ser Ser Ser Gln Asp Ser Cys Ile Ser Met Arg Gln Ser Gly Cys
            340                 345                 350

Leu Pro Leu Leu Ile Gln Leu Leu His Gly Asn Asp Lys Asp Ser Val
            355                 360                 365

Leu Leu Gly Asn Ser Arg Gly Ser Lys Glu Ala Arg Ala Arg Ala Ser
370                 375                 380

Ala Ala Leu His Asn Ile Ile His Ser Gln Pro Asp Asp Lys Arg Gly
385                 390                 395                 400

Arg Arg Glu Ile Arg Val Leu His Leu Leu Glu Gln Ile Arg Ala Tyr
                405                 410                 415
```

```
Cys Glu Thr Cys Trp Glu Trp Gln Glu Ala His Glu Pro Gly Met Asp
            420                 425                 430

Gln Asp Lys Asn Pro Met Pro Ala Pro Val Glu His Gln Ile Cys Pro
            435                 440                 445

Ala Val Cys Val Leu Met Lys Leu Ser Phe Asp Glu His Arg His
450                 455                 460

Ala Met Asn Glu Leu Gly Gly Leu Gln Ala Ile Ala Glu Leu Leu Gln
465                 470                 475                 480

Val Asp Cys Glu Met Tyr Gly Leu Thr Asn Asp His Tyr Ser Ile Thr
                485                 490                 495

Leu Arg Arg Tyr Ala Gly Met Ala Leu Thr Asn Leu Thr Phe Gly Asp
                500                 505                 510

Val Ala Asn Lys Ala Thr Leu Cys Ser Met Lys Gly Cys Met Arg Ala
                515                 520                 525

Leu Val Ala Gln Leu Lys Ser Glu Ser Glu Asp Leu Gln Gln Val Ile
530                 535                 540

Ala Ser Val Leu Arg Asn Leu Ser Trp Arg Ala Asp Val Asn Ser Lys
545                 550                 555                 560

Lys Thr Leu Arg Glu Val Gly Ser Val Lys Ala Leu Met Glu Cys Ala
                565                 570                 575

Leu Glu Val Lys Lys Glu Ser Thr Leu Lys Ser Val Leu Ser Ala Leu
                580                 585                 590

Trp Asn Leu Ser Ala His Cys Thr Glu Asn Lys Ala Asp Ile Cys Ala
            595                 600                 605

Val Asp Gly Ala Leu Ala Phe Leu Val Gly Thr Leu Thr Tyr Arg Ser
610                 615                 620

Gln Thr Asn Thr Leu Ala Ile Ile Glu Ser Gly Gly Gly Ile Leu Arg
625                 630                 635                 640

Asn Val Ser Ser Leu Ile Ala Thr Asn Glu Asp His Arg Gln Ile Leu
                645                 650                 655

Arg Glu Asn Asn Cys Leu Gln Thr Leu Leu Gln His Leu Lys Ser His
                660                 665                 670

Ser Leu Thr Ile Val Ser Asn Ala Cys Gly Thr Leu Trp Asn Leu Ser
            675                 680                 685

Ala Arg Asn Pro Lys Asp Gln Glu Ala Leu Trp Asp Met Gly Ala Val
690                 695                 700

Ser Met Leu Lys Asn Leu Ile His Ser Lys His Lys Met Ile Ala Met
705                 710                 715                 720

Gly Ser Ala Ala Ala Leu Arg Asn Leu Met Ala Asn Arg Pro Ala Lys
                725                 730                 735

Tyr Lys Asp Ala Asn Ile Met Ser Pro Gly Ser Ser Leu Pro Ser Leu
                740                 745                 750

His Val Arg Lys Gln Lys Ala Leu Glu Ala Glu Leu Asp Ala Gln His
                755                 760                 765

Leu Ser Glu Thr Phe Asp Asn Ile Asp Asn Leu Ser Pro Lys Ala Ser
770                 775                 780

His Arg Ser Lys Gln Arg His Lys Gln Ser Leu Tyr Gly Asp Tyr Val
785                 790                 795                 800

Phe Asp Thr Asn Arg His Asp Asp Asn Arg Ser Asp Asn Phe Asn Thr
                805                 810                 815

Gly Asn Met Thr Val Leu Ser Pro Tyr Leu Asn Thr Thr Val Leu Pro
                820                 825                 830

Ser Ser Ser Ser Ser Arg Gly Ser Leu Asp Ser Ser Arg Ser Glu Lys
                835                 840                 845
```

```
Asp Arg Ser Leu Glu Arg Glu Arg Gly Ile Gly Leu Gly Asn Tyr His
850                 855                 860

Pro Ala Thr Glu Asn Pro Gly Thr Ser Ser Lys Arg Gly Leu Gln Ile
865                 870                 875                 880

Ser Thr Thr Ala Ala Gln Ile Ala Lys Val Met Glu Glu Val Ser Ala
                885                 890                 895

Ile His Thr Ser Gln Glu Asp Arg Ser Ser Gly Ser Thr Thr Glu Leu
            900                 905                 910

His Cys Val Thr Asp Glu Arg Asn Ala Leu Arg Arg Ser Ser Ala Ala
        915                 920                 925

His Thr His Ser Asn Thr Tyr Asn Phe Thr Lys Ser Glu Asn Ser Asn
    930                 935                 940

Arg Thr Cys Ser Met Pro Tyr Ala Lys Leu Glu Tyr Lys Arg Ser Ser
945                 950                 955                 960

Asn Asp Ser Leu Asn Ser Val Ser Ser Asn Asp Gly Tyr Gly Lys Arg
                965                 970                 975

Gly Gln Met Lys Pro Ser Ile Glu Ser Tyr Ser Glu Asp Asp Glu Ser
            980                 985                 990

Lys Phe Cys Ser Tyr Gly Gln Tyr Pro Ala Asp Leu Ala His Lys Ile
        995                 1000                1005

His Ser Ala Asn His Met Asp Asp Asn Asp Gly Glu Leu Asp Thr Pro
    1010                1015                1020

Ile Asn Tyr Ser Leu Lys Tyr Ser Asp Glu Gln Leu Asn Ser Gly Arg
1025                1030                1035                1040

Gln Ser Pro Ser Gln Asn Glu Arg Trp Ala Arg Pro Lys His Ile Ile
                1045                1050                1055

Glu Asp Glu Ile Lys Gln Ser Glu Gln Arg Gln Ser Arg Asn Gln Ser
            1060                1065                1070

Thr Thr Tyr Pro Val Tyr Thr Glu Ser Thr Asp Asp Lys His Leu Lys
        1075                1080                1085

Phe Gln Pro His Phe Gly Gln Gln Glu Cys Val Ser Pro Tyr Arg Ser
    1090                1095                1100

Arg Gly Ala Asn Gly Ser Glu Thr Asn Arg Val Gly Ser Asn His Gly
1105                1110                1115                1120

Ile Asn Gln Asn Val Ser Gln Ser Leu Cys Gln Glu Asp Asp Tyr Glu
                1125                1130                1135

Asp Asp Lys Pro Thr Asn Tyr Ser Glu Arg Tyr Ser Glu Glu Glu Gln
            1140                1145                1150

His Glu Glu Glu Arg Pro Thr Asn Tyr Ser Ile Lys Tyr Asn Glu
        1155                1160                1165

Glu Lys Arg His Val Asp Gln Pro Ile Asp Tyr Ser Leu Lys Tyr Ala
    1170                1175                1180

Thr Asp Ile Pro Ser Ser Gln Lys Gln Ser Phe Ser Phe Ser Lys Ser
1185                1190                1195                1200

Ser Ser Gly Gln Ser Ser Lys Thr Glu His Met Ser Ser Ser Ser Glu
                1205                1210                1215

Asn Thr Ser Thr Pro Ser Ser Asn Ala Lys Arg Gln Asn Gln Leu His
            1220                1225                1230

Pro Ser Ser Ala Gln Ser Arg Ser Gly Gln Pro Gln Lys Ala Ala Thr
        1235                1240                1245

Cys Lys Val Ser Ser Ile Asn Gln Glu Thr Ile Gln Thr Tyr Cys Val
    1250                1255                1260

Glu Asp Thr Pro Ile Cys Phe Ser Arg Cys Ser Ser Leu Ser Ser Leu
```

-continued

```
                 1265                1270                1275                1280
Ser Ser Ala Glu Asp Glu Ile Gly Cys Asn Gln Thr Thr Gln Glu Ala
                 1285                1290                1295

Asp Ser Ala Asn Thr Leu Gln Ile Ala Glu Ile Lys Gly Lys Ile Gly
                 1300                1305                1310

Thr Arg Ser Ala Glu Asp Pro Val Ser Glu Val Pro Ala Val Ser Gln
                 1315                1320                1325

His Pro Arg Thr Lys Ser Ser Arg Leu Gln Gly Ser Ser Leu Ser Ser
                 1330                1335                1340

Glu Ser Ala Arg His Lys Ala Val Glu Phe Pro Ser Gly Ala Lys Ser
1345                1350                1355                1360

Pro Ser Lys Ser Gly Ala Gln Thr Pro Lys Ser Pro Pro Glu His Tyr
                 1365                1370                1375

Val Gln Glu Thr Pro Leu Met Phe Ser Arg Cys Thr Ser Val Ser Ser
                 1380                1385                1390

Leu Asp Ser Phe Glu Ser Arg Ser Ile Ala Ser Ser Val Gln Ser Glu
                 1395                1400                1405

Pro Cys Ser Gly Met Val Ser Gly Ile Ile Ser Pro Ser Asp Leu Pro
                 1410                1415                1420

Asp Ser Pro Gly Gln Thr Met Pro Pro Ser Arg Ser Lys Thr Pro Pro
1425                1430                1435                1440

Pro Pro Pro Gln Thr Ala Gln Thr Lys Arg Glu Val Pro Lys Asn Lys
                 1445                1450                1455

Ala Pro Thr Ala Glu Lys Arg Glu Ser Gly Pro Lys Gln Ala Ala Val
                 1460                1465                1470

Asn Ala Ala Val Gln Arg Val Gln Val Leu Pro Asp Ala Asp Thr Leu
                 1475                1480                1485

Leu His Phe Ala Thr Glu Ser Thr Pro Asp Gly Phe Ser Cys Ser Ser
                 1490                1495                1500

Ser Leu Ser Ala Leu Ser Leu Asp Glu Pro Phe Ile Gln Lys Asp Val
1505                1510                1515                1520

Glu Leu Arg Ile Met Pro Pro Val Gln Glu Asn Asp Asn Gly Asn Glu
                 1525                1530                1535

Thr Glu Ser Glu Gln Pro Lys Glu Ser Asn Glu Asn Gln Glu Lys Glu
                 1540                1545                1550

Ala Glu Lys Thr Ile Asp Ser Glu Lys Asp Leu Leu Asp Asp Ser Asp
                 1555                1560                1565

Asp Asp Asp Ile Glu Ile Leu Glu Glu Cys Ile Ile Ser Ala Met Pro
                 1570                1575                1580

Thr Lys Ser Ser Arg Lys Gly Lys Lys Pro Ala Gln Thr Ala Ser Lys
1585                1590                1595                1600

Leu Pro Pro Pro Val Ala Arg Lys Pro Ser Gln Leu Pro Val Tyr Lys
                 1605                1610                1615

Leu Leu Pro Ser Gln Asn Arg Leu Gln Pro Gln Lys His Val Ser Phe
                 1620                1625                1630

Thr Pro Gly Asp Asp Met Pro Arg Val Tyr Cys Val Glu Gly Thr Pro
                 1635                1640                1645

Ile Asn Phe Ser Thr Ala Thr Ser Leu Ser Asp Leu Thr Ile Glu Ser
                 1650                1655                1660

Pro Pro Asn Glu Leu Ala Ala Gly Glu Gly Val Arg Gly Gly Ala Gln
1665                1670                1675                1680

Ser Gly Glu Phe Glu Lys Arg Asp Thr Ile Pro Thr Glu Gly Arg Ser
                 1685                1690                1695
```

```
Thr Asp Glu Ala Gln Gly Gly Lys Thr Ser Ser Val Thr Ile Pro Glu
        1700                1705                1710

Leu Asp Asp Asn Lys Ala Glu Glu Gly Asp Ile Leu Ala Glu Cys Ile
            1715                1720                1725

Asn Ser Ala Met Pro Lys Gly Lys Ser His Lys Pro Phe Arg Val Lys
        1730                1735                1740

Lys Ile Met Asp Gln Val Gln Gln Ala Ser Ala Ser Ser Ser Ala Pro
1745                1750                1755                1760

Asn Lys Asn Gln Leu Asp Gly Lys Lys Lys Pro Thr Ser Pro Val
        1765                1770                1775

Lys Pro Ile Pro Gln Asn Thr Glu Tyr Arg Thr Arg Val Arg Lys Asn
        1780                1785                1790

Ala Asp Ser Lys Asn Asn Leu Asn Ala Glu Arg Val Phe Ser Asp Asn
        1795                1800                1805

Lys Asp Ser Lys Lys Gln Asn Leu Lys Asn Asn Ser Lys Asp Phe Asn
        1810                1815                1820

Asp Lys Leu Pro Asn Asn Glu Asp Arg Val Arg Gly Ser Phe Ala Phe
1825                1830                1835                1840

Asp Ser Pro His His Tyr Thr Pro Ile Glu Gly Thr Pro Tyr Cys Phe
                1845                1850                1855

Ser Arg Asn Asp Ser Leu Ser Ser Leu Asp Phe Asp Asp Asp Val
        1860                1865                1870

Asp Leu Ser Arg Glu Lys Ala Glu Leu Arg Lys Ala Lys Glu Asn Lys
        1875                1880                1885

Glu Ser Glu Ala Lys Val Thr Ser His Thr Glu Leu Thr Ser Asn Gln
        1890                1895                1900

Gln Ser Ala Asn Lys Thr Gln Ala Ile Ala Lys Gln Pro Ile Asn Arg
1905                1910                1915                1920

Gly Gln Pro Lys Pro Ile Leu Gln Lys Gln Ser Thr Phe Pro Gln Ser
                1925                1930                1935

Ser Lys Asp Ile Pro Asp Arg Gly Ala Ala Thr Asp Glu Lys Leu Gln
        1940                1945                1950

Asn Phe Ala Ile Glu Asn Thr Pro Val Cys Phe Ser His Asn Ser Ser
        1955                1960                1965

Leu Ser Ser Leu Ser Asp Ile Asp Gln Glu Asn Asn Lys Glu Asn
        1970                1975                1980

Glu Pro Ile Lys Glu Thr Glu Pro Pro Asp Ser Gln Gly Glu Pro Ser
1985                1990                1995                2000

Lys Pro Gln Ala Ser Gly Tyr Ala Pro Lys Ser Phe His Val Glu Asp
                2005                2010                2015

Thr Pro Val Cys Phe Ser Arg Asn Ser Ser Leu Ser Ser Leu Ser Ile
                2020                2025                2030

Asp Ser Glu Asp Asp Leu Leu Gln Glu Cys Ile Ser Ser Ala Met Pro
        2035                2040                2045

Lys Lys Lys Lys Pro Ser Arg Leu Lys Gly Asp Asn Glu Lys His Ser
2050                2055                2060

Pro Arg Asn Met Gly Gly Ile Leu Gly Glu Asp Leu Thr Leu Asp Leu
2065                2070                2075                2080

Lys Asp Ile Gln Arg Pro Asp Ser Glu His Gly Leu Ser Pro Asp Ser
                2085                2090                2095

Glu Asn Phe Asp Trp Lys Ala Ile Gln Glu Gly Ala Asn Ser Ile Val
                2100                2105                2110

Ser Ser Leu His Gln Ala Ala Ala Ala Cys Leu Ser Arg Gln Ala
        2115                2120                2125
```

```
Ser Ser Asp Ser Asp Ser Ile Leu Ser Leu Lys Ser Gly Ile Ser Leu
    2130            2135                2140

Gly Ser Pro Phe His Leu Thr Pro Asp Gln Glu Glu Lys Pro Phe Thr
2145            2150                2155                2160

Ser Asn Lys Gly Pro Arg Ile Leu Lys Pro Gly Glu Lys Ser Thr Leu
            2165                2170                2175

Glu Thr Lys Lys Ile Glu Ser Ser Lys Gly Ile Lys Gly Gly Lys
    2180                2185                2190

Lys Val Tyr Lys Ser Leu Ile Thr Gly Lys Val Arg Ser Asn Ser Glu
        2195                2200                2205

Ile Ser Gly Gln Met Lys Gln Pro Leu Gln Ala Asn Met Pro Ser Ile
    2210                2215                2220

Ser Arg Gly Arg Thr Met Ile His Ile Pro Gly Val Arg Asn Ser Ser
2225            2230                2235                2240

Ser Ser Thr Ser Pro Val Ser Lys Lys Gly Pro Pro Leu Lys Thr Pro
            2245                2250                2255

Ala Ser Lys Ser Pro Ser Glu Gly Gln Thr Ala Thr Thr Ser Pro Arg
        2260                2265                2270

Gly Ala Lys Pro Ser Val Lys Ser Glu Leu Ser Pro Val Ala Arg Gln
        2275                2280                2285

Thr Ser Gln Ile Gly Gly Ser Ser Lys Ala Pro Ser Arg Ser Gly Ser
    2290                2295                2300

Arg Asp Ser Thr Pro Ser Arg Pro Ala Gln Gln Pro Leu Ser Arg Pro
2305            2310                2315                2320

Ile Gln Ser Pro Gly Arg Asn Ser Ile Ser Pro Gly Arg Asn Gly Ile
            2325                2330                2335

Ser Pro Pro Asn Lys Leu Ser Gln Leu Pro Arg Thr Ser Ser Pro Ser
            2340                2345                2350

Thr Ala Ser Thr Lys Ser Ser Gly Ser Gly Lys Met Ser Tyr Thr Ser
        2355                2360                2365

Pro Gly Arg Gln Met Ser Gln Gln Asn Leu Thr Lys Gln Thr Gly Leu
    2370                2375                2380

Ser Lys Asn Ala Ser Ser Ile Pro Arg Ser Glu Ser Ala Ser Lys Gly
2385                2390                2395                2400

Leu Asn Gln Met Asn Asn Gly Asn Gly Ala Asn Lys Lys Val Glu Leu
            2405                2410                2415

Ser Arg Met Ser Ser Thr Lys Ser Ser Gly Ser Glu Ser Asp Arg Ser
            2420                2425                2430

Glu Arg Pro Val Leu Val Arg Gln Ser Thr Phe Ile Lys Glu Ala Pro
        2435                2440                2445

Ser Pro Thr Leu Arg Arg Lys Leu Glu Glu Ser Ala Ser Phe Glu Ser
    2450                2455                2460

Leu Ser Pro Ser Ser Arg Pro Ala Ser Pro Thr Arg Ser Gln Ala Gln
2465                2470                2475                2480

Thr Pro Val Leu Ser Pro Ser Leu Pro Asp Met Ser Leu Ser Thr His
            2485                2490                2495

Ser Ser Val Gln Ala Gly Gly Trp Arg Lys Leu Pro Pro Asn Leu Ser
            2500                2505                2510

Pro Thr Ile Glu Tyr Asn Asp Gly Arg Pro Ala Lys Arg His Asp Ile
        2515                2520                2525

Ala Arg Ser His Ser Glu Ser Pro Ser Arg Leu Pro Ile Asn Arg Ser
    2530                2535                2540

Gly Thr Trp Lys Arg Glu His Ser Lys His Ser Ser Ser Leu Pro Arg
```

```
                    2545                2550                2555                2560
Val Ser Thr Trp Arg Arg Thr Gly Ser Ser Ser Ile Leu Ser Ala
                2565                2570                2575

Ser Ser Glu Ser Ser Glu Lys Ala Lys Ser Glu Asp Glu Lys His Val
            2580                2585                2590

Asn Ser Ile Ser Gly Thr Lys Gln Ser Lys Glu Asn Gln Val Ser Ala
            2595                2600                2605

Lys Gly Thr Trp Arg Lys Ile Lys Glu Asn Glu Phe Ser Pro Thr Asn
            2610                2615                2620

Ser Thr Ser Gln Thr Val Ser Ser Gly Ala Thr Asn Gly Ala Glu Ser
2625                2630                2635                2640

Lys Thr Leu Ile Tyr Gln Met Ala Pro Ala Val Ser Lys Thr Glu Asp
                2645                2650                2655

Val Trp Val Arg Ile Glu Asp Cys Pro Ile Asn Asn Pro Arg Ser Gly
                2660                2665                2670

Arg Ser Pro Thr Gly Asn Thr Pro Pro Val Ile Asp Ser Val Ser Glu
            2675                2680                2685

Lys Ala Asn Pro Asn Ile Lys Asp Ser Lys Asp Asn Gln Ala Lys Gln
            2690                2695                2700

Asn Val Gly Asn Gly Ser Val Pro Met Arg Thr Val Gly Leu Glu Asn
2705                2710                2715                2720

Arg Leu Thr Ser Phe Ile Gln Val Asp Ala Pro Asp Gln Lys Gly Thr
                2725                2730                2735

Glu Ile Lys Pro Gly Gln Asn Asn Pro Val Pro Val Ser Glu Thr Asn
                2740                2745                2750

Glu Ser Pro Ile Val Glu Arg Thr Pro Phe Ser Ser Ser Ser Ser Ser
            2755                2760                2765

Lys His Ser Ser Pro Ser Gly Thr Val Ala Ala Arg Val Thr Pro Phe
    2770                2775                2780

Asn Tyr Asn Pro Ser Pro Arg Lys Ser Ser Ala Asp Ser Thr Ser Ala
2785                2790                2795                2800

Arg Pro Ser Gln Ile Pro Thr Pro Val Asn Asn Asn Thr Lys Lys Arg
                2805                2810                2815

Asp Ser Lys Thr Asp Ser Thr Glu Ser Ser Gly Thr Gln Ser Pro Lys
            2820                2825                2830

Arg His Ser Gly Ser Tyr Leu Val Thr Ser Val
        2835                2840

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

CAAGGGAATT CAAGGATG                                                        18

(2) INFORMATION FOR SEQ ID NO:4:

(i) SEQUENCE CHARACTERISTICS:
        (A) LENGTH: 19 base pairs
```

```
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

TGCTTCTGTT GCTTGAGGC                                                    19
```

ANTIBODIES AND ASSAY FOR DETECTING MUTANT APC PROTEINS

This application is a continuation of application Ser. No. 08/034,850, filed Mar. 19, 1993, now abandoned.

This invention was made with government support under NIH grant CA-57345 awarded by the National Institutes of Health. The government has certain rights in this invention.

TECHNICAL FIELD OF THE INVENTION

This invention relates to the field of medical diagnostics, in particular to diagnoses of an inherited predisposition to develop cancer.

BACKGROUND OF THE INVENTION

Familial Adenomatous Polyposis (FAP) is an autosomal dominant disease in which affected individuals develop hundreds to thousands of benign colorectal tumors (adenomas). Some of these tumors, if not removed, invariably progress to malignancy (carcinomas). Recently, a candidate tumor suppressor gene from chromosome 5q21, APC[1], was isolated and implicated in the development of FAP (Kinzler, K. W. et al., Science 253:661–665 (1991); Nishisho, I., et al., Science 253:665–669 (1991); Groden, J., et al., Cell 66:589–600 (1991); Joslyn, G., et al., Cell 66:601–613 (1991)). Further analyses of the APC gene in 150 kindreds indicate that APC mutations can account for most if not all cases of FAP (Miyoshi, Y., et al., Proc. Natl. Acad. Sci. USA 89:4452–4456 (1992)).

Carcinomas in FAP patients, however, account for less than 1% of all colorectal cancers. Most colorectal cancers do not have a well recognized inherited basis and therefore are classified as sporadic. Recent studies have indicated that the majority of these sporadic tumors have somatic mutations of the APC gene (Miyoshi, Y., et al., Human Molecular Genetics 1: 229–233 (1992); Powell, S. M., et al., Nature 17:235–237 (1992)). Furthermore, these mutations appear to occur early during colorectal tumorigenesis and have been detected in tumors as small as 0.5 cm in diameter (Powell, S. M., et al., Nature 17:235–237 (1992)). The nature of the mutations identified in sporadic tumors and in FAP patients is striking, with greater than 94% of the mutations predicted to result in truncation of the APC gene product. Taken together, the above studies indicate that APC plays an important and early role in the development of the major forms of colorectal neoplasia.

The APC gene contains an 8,538 bp open reading frame (ORF) and is predicted to encode a 2,843 amino acid polypeptide with few homologies to other proteins (Kinzler, K. W., et al., Science 253:661–665 (1991); Groden, J., et al., Cell 66:589–600 (1991)). The large size of the APC coding region makes identification of mutations in patients labor intensive and costly. Therefore, there is a need in the art for a quicker, less expensive method for identifying patients who carry a mutant APC allele.

SUMMARY OF THE INVENTION

It is an object of the invention to provide an antibody which can detect full-length and truncated forms of the human APC protein.

It is another object of the invention to provide an antibody which can detect full-length but not truncated forms of the human APC protein.

It is still another object of the invention to provide a method for determining the presence of mutations in a human APC gene by determining the size of the APC proteins produced in a tissue.

It is yet another object of the invention to provide an immunohistochemical method for determining the presence of APC mutations in a body sample by comparing the amount of binding of two antibodies which bind to APC in different portions of the protein.

It is another object of the invention to provide an enzyme-linked immunosorbent assay method for determining the presence of APC mutations.

It is still another object of the invention to provide an enzyme-linked immunosorbent assay method for determining the presence of APC mutations in a body sample by comparing the amount of binding of two antibodies which bind to APC in different portions of the protein.

It is another object of the invention to provide a method for determining the presence of an APC mutation by looking for loss of reactivity to a single antibody to APC protein.

It is an object of the invention to provide solid supports for use in performing enzyme-linked immunosorbent assays.

It is another object of the invention to provide hybridoma cells which produce antibodies useful for assaying APC proteins.

These and other objects of the invention are provided by one or more of the embodiments which are described below. In one embodiment of the invention, an antibody preparation is provided in which the antibodies are specifically immunoreactive with an epitope contained within the amino terminal 1103 amino acids of APC.

In another embodiment of the invention, an antibody preparation is provided in which the antibodies are specifically immunoreactive with an epitope contained within the carboxy terminal 306 amino acids of APC.

In still another embodiment of the invention a method for determining the presence of mutations in a human APC gene is provided. The method comprises the following steps: extracting proteins from a human body sample; separating said extracted proteins on a polyacrylamide gel; blotting said separated proteins onto a filter; contacting said filter with antibodies which are specifically immunoreactive with APC protein to bind said antibodies to proteins blotted on said filter; detecting the location of said antibodies which bind to said proteins; determining the size of the proteins which are bound to said antibodies, wherein a size of less than about 300 kDa indicates the presence of an APC mutation in the tissue sample.

In still another embodiment of the invention, a method for determining the presence of APC mutations in a human is provided. The method comprises: contacting a first sample of a tissue or body fluid with a first antibody which is specifically immunoreactive with an epitope contained within the amino terminal 1103 amino acids of APC; determining the amount of binding of the first antibody to said first tissue sample or body fluid; contacting a second sample of the tissue or body fluid with a second antibody which is specifically immunoreactive with an epitope contained within the carboxy terminal 306 amino acids of APC; determining the amount of binding of the second antibody to said second tissue or body fluid sample; comparing the determined amount of binding of said first antibody to the determined amount of binding of said second antibody, wherein finding a tissue or body fluid which binds substantially more of the first antibody than the second antibody indicates the presence of an APC mutation in the human.

In yet another embodiment of the present invention an enzyme-linked immunosorbent assay (ELISA) is provided for determining the presence of APC mutations. The method comprises the steps of: coating a solid support with a first antibody which is specifically immunoreactive with a first epitope, said epitope being contained within the amino terminal 1103 amino acids of APC or the carboxy terminal 306 amino acids of APC; contacting the coated solid support with an aliquot of test sample comprising a body fluid or lysate of a tissue to bind components of said aliquot to said solid support by means of said first antibody; contacting the solid support-bound components of said test sample with a second antibody which is specifically immunoreactive with a second epitope on APC, to bind said second antibody to said solid support by means of said components and said first antibody; determining the amount of second antibody which is bound to said solid support. Alternatively, the test sample comprising a body fluid or tissue lysate can be coated directly onto a solid support without use of a first antibody.

In another embodiment of the invention a method for determining the presence of an APC mutation in a human is provided. The method comprises the steps of: contacting a first tissue sample with an antibody which is specifically immunoreactive with an epitope contained within the carboxy terminal 306 amino acids of APC (as shown in SEQ ID NO:2); and determining the amount of binding of said antibody to said first tissue sample, a tissue which fails to bind the antibody indicating an APC mutation in the human.

In yet another embodiment of the invention a method for detecting truncated forms of APC is provided. The method comprises the steps of: lysing a test sample of cells from a human; fractionating said cells into a soluble and a particulate fraction; contacting said soluble fraction with an antibody which is specifically immunoreactive with an epitope contained within the amino terminal 1103 amino acids of APC (as shown in SEQ ID NO:2); detecting any of said antibody which bound to said soluble fraction, the presence of antibody bound to the soluble fraction indicating a truncated form of APC in said cells.

In still another embodiment of the invention hybridoma cells are provided which secrete an antibody which is specifically immunoreactive with an epitope contained within the amino terminal 1103 amino acids of APC or with an epitope contained within the carboxy terminal 306 amino acids of APC.

These and other embodiments of the invention provide the art with less expensive and less labor intensive means for detecting mutations in APC than are provided by genetic techniques currently available.

BRIEF DESCRIPTION OF THE DRAWINGS

FIG. 3A shows the results obtained with SW480 cells, and FIG. 3B shows the results obtained with a lymphoblastoid cell line derived from a patient heterozygous for a truncating mutation at codon 1309 of APC. For both panels, equivalent proportions of the total protein lysate (lane 1), the 100,000×g insoluble "membrane fraction" (lane 2), the "nuclear fraction" (lane 3) and the "cytoplasmic fraction" (lane 4) were loaded. Full length protein is indicated by "FL" while mutant truncated protein is indicated by "MT".

DETAILED DESCRIPTION OF THE INVENTION

Figure 1A:
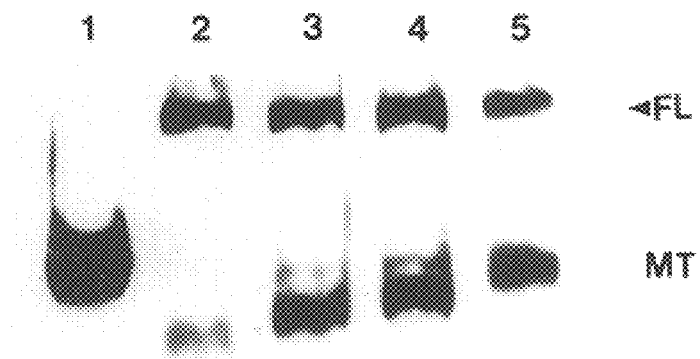
FIGS. 1A, 1B, and 1C show the detection of APC protein by Western blot analysis. Total protein lysates (100 µg) were assayed by Western blot with either polyclonal Anti-NAPC (FIG. 1A), polyclonal Anti-MAPC (FIG. 1B), or monoclonal FE9 (FIG. 1C). Protein lysates were made from the colorectal carcinoma line SW480 containing a stop codon in APC at 1338 (lanes 1) and four different FAP lymphoblastoid cell lines with known truncating APC mutations at codons 1061, 1175, 1211, or 1309 respectively (lanes 2–5). Full length protein is indicated as "FL" while mutant truncated proteins are indicated as "MT".

We have found that the presence of many mutations in the APC gene can be identified in human tissues using immunological methods. Studies utilizing DNA-based analyses of leukocytes of FAP patients have shown that greater than 90% of the mutations are predicted to result in truncations of the APC protein. (Miyoshi et al., *Proc. Natl. Acad. Sci.*, 89:4452, 1992.) Other studies of primary, sporadic, colorectal tumors indicate that at least 60% of colorectal tumors contain truncating APC mutations (Miyoshi, et al., *Human Molecular Genetics*, 1:229–233 (1992); Powell, et al., *Nature*, 17:235–237 (1992)). These mutations include point mutations which generate stop codons, and deletions and insertions which generate frameshifts which create stop codons immediately downstream from the mutations. In accordance with the present invention, an antibody specifically immunoreactive with an epitope contained within the amino terminal 1103 amino acids of APC detects truncated APC proteins and can be used to detect the majority of both inherited and somatic mutations in the APC gene.

Fusion proteins can and have been made which comprise a portion of the APC protein fused to the carboxyl end of another protein, or portion thereof. These fusion proteins are obtained by expressing gene fusions of the protein coding regions. Any other protein can be used to fuse with APC. Usually the other protein is selected for some desirable property. For example maltose binding protein (MBP) can be used, as it renders the fusion protein easily purified by means of an amylose column. The bacterial gene trpE can also be used advantageously, as it is inducible by means of tryptophan starvation.

Portions of the APC protein can be selected for fusion to other proteins, as desired. Typically a segment of the large APC protein of about 100–500 amino acid residues is chosen. In a preferred embodiment of the invention an amino terminal segment and optionally a carboxy terminal segment are chosen. For example, in a particular embodiment of the invention a fusion protein is used which comprises APC amino acids 1–220. In another embodiment a peptide which comprises APC amino acids 2537–2843 (the carboxy terminal 306 amino acids) is used. In still another embodiment of the invention a peptide which comprises amino acids 221 to 1103 of APC is used.

The fusion proteins can be used to immunize animals in order to obtain antibodies specifically immunoreactive with epitopes contained within the chosen fragment. Antisera of the immunized animals can be collected and optionally affinity purified. It is desirable to use as an affinity reagent either the fusion protein which was used to immunize the animals, or preferably a fusion protein having the same portion of APC protein, but having a different amino terminal protein. Affinity purification of polyclonal antibodies is well known in the art, and can be accomplished using routine methods.

Fusion proteins are not the only immunogens which can be used to raise the antibodies of the present invention. Synthetic, recombinant, or naturally produced peptides containing amino acid sequences of the APC protein can be used alone, or linked to other proteins, such as keyhole limpet hemocyanin (KLH), to generate a sufficient immune response. Other means of administering an immunogen to bolster the immune response may be used, as are known in the art.

Spleen cells of the immunized animals may also be fused to myeloma cells, according to the method of Kohler and Milstein, to generate hybridoma cells which secrete monoclonal antibodies. The hybridoma cells can be screened for production of appropriate antibodies by use of the original immunogen, or another form of an immunogen which contains the same, or an overlapping portion of the APC protein. Cloning and subcloning of the hybridoma cells is accomplished, as is known in the art, to achieve a cell line which stably produces antibodies which are specifically immunoreactive with epitopes on APC protein. Specific immunoreactivity means that the antibodies do not bind to other human proteins.

Particular monoclonal antibodies which have been found to be useful in the practice of the present invention are listed in Tables I and II. Not all of the antibodies which will immunoprecipitate APC will bind to APC on Western blot. This may be due to conformational epitopes which are destroyed under conditions of SDS-polyacrylamide gel electrophoresis. Other antibodies which can neither immunoprecipitate nor detect APC on Western blots can detect APC by immunohistocheinistry, e.g., on cryostat sections.

In one method according to the present invention APC mutations are detected by running proteins extracted from a test sample on an SDS-PAGE. Samples for testing according to the present invention are any tissue, whether suspected of being neoplastic or not. Also useful are body fluids, such as urine, blood, serum, plasma, fecal material, saliva, etc. Either cells or shed antigen, can be detected in such body fluids. Lysates of cells are also useful. The proteins are blotted onto filters and the blotted proteins are then contacted with one of the antibodies of the present invention (Western blotting). Antibodies which bind to blotted proteins are detected by an appropriate staining technique. The size of the proteins which have bound proteins is determined. If the protein which binds to antibody has a size less than about 300 kDa, this is an indication that there is an APC mutation in the tissue sample which is a "truncation mutation", typically a nonsense, frameshifting deletion, or frameshifting insertion mutation. In order to detect the maximum number of such truncation mutations, it is desirable to use an antibody which specifically immunoreacts with an epitope in the amino terminal portion of the protein. Use of a carboxy terminal epitope-binding antibody could result in the failure to detect truncation proteins which are actually present in the tissue.

Although small truncation proteins may be adequately detected using standard Western blotting techniques, larger truncation proteins and full length APC protein may fail to be sufficiently blotted from an SDS-PAGE due to their large size. Therefore it is desirable to use techniques which lead to enhanced transfer from gel matrix to filter. These may include, for example, the use of 3% low melting point agarose to form the gel matrix.

According to the present invention, patients can be tested to determine whether they have inherited a germ-line mutation of APC, or to determine somatic mutations. In the former case, a suitable and convenient tissue sample comprises peripheral blood mononuclear cells or leukocytes. If a germ-line mutation is present, it can be detected in any tissue of the body. In the latter case (somatic mutations), the test tissue sample should comprise tumor tissue or preneoplastic tissue. A control sample comprising non-tumor tissue, preferably of adjacent noncancerous tissue, can also be tested.

In an alternative method for detecting APC mutations according to the present invention, immunohistochemistry or immunofluorescence is employed. A tissue sample or cell sample is prepared by any standard technique known in the art. Peripheral blood mononuclear cells can be fixed according to known techniques for immunochemical staining. Tissue samples can be frozen and embedded in a mounting compound, for example O.C.T. (Miles Laboratories). Thin sections can then be cut, incubated with an antibody specific for APC, stained, and observed. According to one method, an antibody which is immunoreactive with an epitope contained within the amino terminal portion of APC is used to stain a first sample of a tissue. A second antibody which is specifically immunoreactive with an epitope contained within the carboxy terminal portion of APC is used to stain a second sample of the same tissue. The amount of binding of each antibody is determined. If substantially more of the amino terminal antibody binds to the tissue sample than does the carboxy terminal antibody, an APC truncation mutation is indicated. In one embodiment of the invention antibodies are used which are labelled with a detectable tag, such as an immunofluorescent compound or radioactive molecule. Such a detectable tag can also be attached to an additional antibody which is immunoreactive with the amino terminal or carboxy terminal anti-APC antibodies. In another embodiment of the invention an antibody is labelled by linkage to an enzyme which upon contact with an appropriate enzyme substrate, generates a colored reaction product. In still another embodiment of the invention detectable tags are linked to the antibody via an avidin:biotin ligand binding pair, as is generally known in the art. Typically, the antibody is linked to biotin and the detectable tag, e.g., alkaline phosphatase, is conjugated to avidin. According to one aspect of the invention the amino terminal and carboxy terminal antibodies are incubated with the same tissue sample or cell sample. In that case the antibodies are labelled with different detectable tags.

Enzyme-linked immunosorbent assays (ELISA) are also contemplated within the scope of the present invention. Such assays employ solid supports, such as microtiter plates or dipsticks, which are coated with a first antibody which is specifically immunoreactive with an epitope which is contained within the amino terminal portion of APC. A test sample is contacted with the coated solid support under conditions where antigen-antibody complexes form and are stable to allow components of the test sample to bind to the antibody which has been coated onto the support, if such components are present in the test sample. Appropriate washing of the solid support is used, as is known in the art, to remove components of the test sample which are not specifically bound to the antibodies. A second antibody is added which is specifically immunoreactive with a second epitope on APC. Thus the components of the test sample which bound to the first (amino terminal) antibody, are now sandwiched between two antibodies. Second antibody which has not specifically bound to the support-bound components of the test sample are washed away, under conditions in which antigen-antibody complexes which have formed are stable. The amount of second antibody which is bound to the solid support (by means of the first antibody and the components of the test sample) is determined, typically by adding a chromogenic substrate which generates a colored product upon contact with an enzyme which is linked to the second antibody. Alternative formats for running such ELISA assays are contemplated and include binding the test sample directly to the solid support without using a first antibody.

According to another aspect of the present invention, a second aliquot of the test sample may be run through a parallel enzyme-linked immunosorbent assay, as described above. However, in this parallel ELISA different antibodies are coated onto the solid support. In this version, a carboxy terminal antibody is used as the first antibody. Thus when the results of the first and second parallel ELISAs are compared, a substantially smaller amount of binding occurring in the second ELISA than in the first indicates an APC mutation in the tissue from which the sample was derived. Samples can be, for example, lysates of blood cells or of solid tumors. Other assays which can be performed using the antibodies of the present invention include immunoprecipitations, and protein dot blots. The antibodies used in the practice of this invention may be either polyclonal or monoclonal or combinations thereof.

In another aspect of the invention, tissue samples can be analyzed, for example by immunohistochemistry, for the ability to bind to an antibody which is specific for an epitope in the carboxy terminal 306 amino acids of APC. If the tissue sample fails to bind the antibody, then truncation and/or deletion mutations of APC are indicated. If desired, a control sample of an adjacent, normal tissue may be analyzed using the same antibody. The ability of the control sample to bind the antibody when the test sample failed to do so indicates a somatic mutation of APC.

According to still another aspect of the invention, immunological detection is combined with subcellular fractionation to yield information about a human's APC alleles. It has been found that full-length APC protein is found in a particulate fraction, whereas the soluble or cytoplasmic fraction contains only truncated forms. If full-length APC and truncated APC are present in the same cell, the truncated form is also detected in the particulate fraction, presumably due to oligomerization of the APC proteins. Thus if only particulate APC is detected, one infers that the human has two wild-type alleles. If both forms of APC are detected, than one infers that the human has one mutant and one wild-type allele. If only cytosolic APC is observed, then one infers that the human has two mutant alleles of APC. One mutant allele indicates a predisposition to sporadic or familial colon cancer. Two mutant alleles indicate a worse prognosis.

Subcellular fractionation, according to the present invention can be accomplished by any means which separates typically cytoplasmic cellular components from typically membrane-associated cellular components. In one method of accomplishing the fractionation, cells are first lysed (either mechanically or osmotically, for example) and then nuclei and unbroken cells are removed by a slow centrifugation, typically at about 500×g. The supernatant can then be centrifuged at about 100,000×g for 1 hour to pellet the particulate or membrane-associated fraction. The remaining supernatant is considered to be the soluble or cytoplasmic fraction. As stated above, full-length APC has been found in the particulate fraction, whereas truncated APC is found in the soluble fraction. If full-length APC is present in the cell along with truncated APC, then truncated APC also can be found in the particulate fraction.

After subcellular fractionation has been accomplished, the proteins can be analyzed immunologically, by any means taught herein. Typically the proteins of the individual fractions are separated electrophorectically, and immunoblotted. Alternatively, the fractions can be assayed in an ELISA format using both an antibody which binds to the amino terminal portion of APC and optionally an antibody which binds to the carboxy terminal portion of APC.

Antibody-secreting hybridomas according to the present invention have been deposited at the American Type Culture Collection (ATCC), 12301 Parklawn Avenue, Rockville, Md. 20852-1996 on Mar. 11, 1993. These include the antibodies known as FE9, AC4, CC1, CF11, DB1, IA1, IE1, and HG2 which have been given the accession numbers HB 11294, HB 11292, HB 11296, HB 11288, HB 11295, HB 11297, HB 11298, and HB 11293, respectively. Other hybridomas making antibodies which bind to the same epitopes can be made, e.g., using anti-idiotype technology. Antibodies can be tested for binding to the same epitope as the deposited antibodies by examining the ability to completely inhibit the binding of the deposited antibody to its cognate antigen. It has been found that FE9 binds to an epitope comprising amino acids 16–29 of APC. AC4 binds to an epitope comprising amino acids 109–170 of APC. Isotype switching variants of these antibodies can also be made, as is known in the art. See e.g., Spira et al., (1985) "The Generation of Better Monoclonal Antibodies Through Somatic Mutations", *Hybridoma Technology in the Biosciences and Medicine* (ed. Springer), pp. 77–78, Plenum Press, N.Y.

Solid supports according to the present invention may be any plastic, paper, or glass to which antibodies will adhere. Most typically solid supports comprise a plastic microtiter plate. Precoated paper sheets and sticks are also contemplated, as well as microspheres, as carriers of the antibodies of the present invention.

The antibodies of the present invention can also be used as imaging agents. They can be labeled, as is known in the art, and administered to a patient to assess tumor load in the colon, or to detect metastases.

The antibodies of the present invention are useful for determining the presence of germ-line or somatic mutations which indicate a predisposition to colon cancer. APC mutations may also be involved in the development of gastric, esophageal, pancreatic and small cell lung cancers. The presence of germ-line APC mutations is associated with FAP and portends a high probability that the patient will develop colon carcinoma. Somatic APC mutations have been found to be associated with the early development of colonic tumors.

EXAMPLES

Example 1

This example demonstrates the construction of bacterial fusion proteins useful for immunizing and screening to obtain antibodies specific for portions of the APC protein.

Bacterial fusion proteins containing the amino terminal portion of the APC protein were constructed from partial APC CDNA clones as follows. A fragment of the APC gene containing nucleotides −15 to 734 was engineered to have an EcoRI site 10 nucleotides 5' of the initiating methionine by PCR amplification with the following primers, 5'-CAAGGGAATTCAAGGATG-3' (SEQ ID NO:3), and 5'TGCTTCTGTTGCTTGAGGC-3' (SEQ ID NO:4); (underlined bases were altered to create the EcoRI site). After digestion with EcoRI, a fragment extending from the engineered EcoRI site to the endogenous EcoRI site at nucleotide 660 was cloned into the EcoRI site of pATH3 (Koerner, T. J., et al., Methods Enzymol. 194:477–490 (1991)) and pGEX-3X (Pharmacia) resulting in a trpE fusion (pATH-NAPC) or a glutathione-S-transferase (GST) fusion (pGEX-NAPC).

A second non-overlapping set of fusion proteins was constructed from an APC EcoRi fragment extending from the endogenous EcoRi site at nucleotide 660 to an exogenous EcoRI site at nucleotide 3309 introduced during cDNA cloning. This fragment was cloned into pATH3, pMAL-C2 (New England Biolabs), and pGEX-2T (Pharmacia) resulting in a trpe fusion (pATH-MAPC), a maltose binding protein (MBP) fusion (MBP-MAPC), or a GST fusion (pGEX-MAPC). The third set of fusion proteins contain the 306 extreme carboxy terminal amino acids of APC cloned into pATH3 and pMAL-C2 expression vectors to give fusion proteins trpE-XC and MBP-XC, respectively. The full length fusion protein (trpE-XC) has a molecular weight of 75 kDa.

The pATH encoded trpE fusion proteins were produced in temperature sensitive E. coli CAG456 (Baker, T. A., et al., Proc. Natl. Acad. Sci. USA 81: 6779–6783 (1984)). Stationary phase E. coli were diluted 1:5 and induced for 12 hr by tryptophan starvation. The cells were harvested by centrifugation and resuspended in 1/60 volume TEN (50 mM Tris HCl (pH 8), 1 mM EDTA, 50 mM NaCl). Lysozyme was added to 20 mg/ml and the culture was incubated on ice for 15 minutes. After addition of NP-40 to a final concentration of 0.25%, the sample was sonicated, the insoluble fusion proteins were pelleted (12,000×g for 5 minutes at 4° C.), washed with TEN, and frozen at −80° C.

The pGEX encoded glutathione-S-transferase fusion proteins were produced in E. coli JM101 cells. Cells were grown at 37° C. to an absorbance ($A_{600}$) of 0.5 at 550 nm and induced by the addition of isopropyl-β-D-thiogalactoside (0.5 mM). After a 4 hour induction, the cells were harvested by centrifugation, resuspended in 1/30 volume MTPBS (150 mM sodium chloride, 16 mM monobasic sodium phosphate and 4 mM dibasic sodium phosphate, pH 7.3) and sonicated. The insoluble fusion proteins were pelleted, washed once with 0.03% SDS and frozen at −80° C.

Soluble forms of the pMAL-C2 encoded maltose binding protein fusion proteins MBP-XC and MBP-MAPC expressed in E. coli cells were produced and purified as follows: Cells were grown at 37° C. to an absorbance ($A^{600}$) of 0.5. Fusion protein expression was then induced by addition of isopropyl-β-D-thiogalactoside to 0.5 mM. After a 4 hour incubation, the cells were harvested by cenyrifugation, resuspended in 1/10 volume of STE (150 mM NaCl, 10 mM Tris-Cl, pH 7.4, and 1 mM EDTA) and passed twice through a 20K French Pressure cell (SLM Aminco, SLM Instruments, Inc. Urbana, Ill.) at 15,000 PSI to break open cells. Insoluble material was removed by centrifugation at 16,000×g for 10 minutes and the remanining soluble material was applied to an amylose column. Soluble MBP-XC and MBP-MAPC were eluted from the column with amylose. Peak fractions were identified by SDS/PAGE and pooled.

Example 2

This example demonstrates the production of polyclonal antibodies specifically immunoreactive with amino or carboxy terminal segments of APC protein.

The insoluble bacterial pellets containing the trpE bacterial fusion proteins were purified by SDS-PAGE. Gel slices containing approximately 300 μg of fusion protein were homogenized in Freund's complete adjuvant (Sigma) for the primary injection and Freund's incomplete adjuvant (Sigma) for booster injections. Two New Zealand white rabbits were injected with each protein preparation. Rabbits were injected every 2 weeks and bled 10 days after each booster injection. The antibodies were affinity purified by binding to the glutathione-S-transferase insoluble bacterial fusion proteins. The bacterial pellets containing 200 μg of fusion protein were thawed, washed with TEN and pelleted. One ml of antisera was added to the pellet and incubated on ice for one hour. The antibody-insoluble protein complexes were then pelleted and washed with TBS. The antibodies were released with 500 μl of 0.2 M glycine, pH 2.3 on ice for five minutes. The remaining insoluble proteins were pelleted. The antibody solution was neutralized with 70 μl of 1M Tris pH 9.5. Bovine serum albumin and sodium azide were added to a final concentration of 5 mg/ml and 0.05%, respectively.

Example 3

This example demonstrates the production of monoclonal antibodies specifically immunoreactive with amino or carboxy terminal segments of APC.

Female CB6/F1 mice were immunized by intraperitoneal injection on three successive occasions with 20 μg of trpE-NAPC or trpE-XC fusion protein which had been expressed in E. coli and purified by electroelution following SDS-PAGE. Hybridomas were produced as described (McKenzie, S. J., et al., Oncogene 4: 543–548 (1989)), except fused cells were plated at a density of 1×10⁶/ml. Mouse test bleeds and hybridomas were screened for anti-APC reactivity by an antigen capture ELISA using purified GST-NAPC (Smith, D. B., et al., Gene 67:31–40 (1988)) or soluble MBP-XC, purified as described above, coated on plates at a concentration of 500 ng/ml or 3 μg/ml, respectively. Purified GST-MDM2, expressed and purified as described (Oliner, J. D., et al., Nature 358:80–83 (1992)) and purified MBP-MAPC were was used as the negative control antigens. Antigen/antibody complexes were detected by incubation with horseradish peroxidase conjugated goat anti-mouse IgG heavy and light chain (Kirkegaard and Perry Labs, Inc.) followed by development with tetramethylbenzidine as described (McKenzie, S. J., et al., Oncogene 4:543–548 (1989)). All positive hybridomas were subcloned twice by limiting dilution. Monoclonal antibodies directed against the amino terminal portion of APC were initially tested for specific recognition of APC by Western blot using GST-NAPC and trpE-NAPC, to show anti-APC reactivity, while GST-MDM2 and trpE-MAPC were used as negative controls. The monoclonal antibodies directed against the carboxy terminal portion of APC were initially tested for specific recognition of APC by ELISA using soluble fusion protein MBP-XC to show anti-APC reactivity and MBP-MAPC as negative control.

Ten hybridomas were isolated which reacted specifically with an epitope contained within amino acids 1–220 of APC. Six hybridomas were isolated which specifically reacted with an epitope contained within the carboxy terminal 306 amino acid residues of APC. These are noted in Tables I and II which also show their isotypes.

TABLE I

Summary of APC-NH Monoclonals

| Antibody | Isotype | Western Blot | Immunoprecipitation |
|---|---|---|---|
| AC4-2F[1] | IgG$_1$ | + | |
| BD2-2E | IgG$_{2a}$ | + | |
| BD12-2I | IgG$_{2b}$ | + | + |
| BE7-2J | IgG$_1$ | + | |
| CC1-2H | IgG$_{2b}$ | + | + |
| CF11-1G | IgG$_{2b}$ | + | + |
| EF4-1H | IgG$_1$ | + | + |
| FC5-1C | IgG$_1$ | + | |
| FE9-1B[2] | IgG$_1$ | + | + |
| HA94-2J | IgG$_1$ | + | |

[1]= AC4 is able to detect APC by immunohistochemistry on cryostat sections.
[2]= FE9 is also able to detect APC by Western blot in cell lines listed in Smith et al.

TABLE II

Summary of APC-XC Monoclonals

| Antibody | Isotype | Western Blot | Immunoprecipitation |
|---|---|---|---|
| DB1-2C | IgG$_1$ | + | + |
| HG2-1C[3] | IgG$_1$ | + | + |
| IA1-1D | IgG$_1$ | + | + |
| IB6-1L | IgG$_1$ | | |
| IE1-2J | IgG$_1$ | + | + |
| IE8-2G | IgG$_1$ | + | + |

[3]= HG2-1C is able to detect APC by immunohistochemistry on cryostat sections.

Example 4

This example demonstrates the characterization of the ten monoclonal antibodies specific for APC amino terminus by Western blot and immunoprecipitation.

For the western blots, 1 µg each of GST-NAPC, GST-MDM-2, trpE-NAPC and trpE-MAPC, were separated by SDS-PAGE and transferred to nitrocellulose. The blots were probed with 10 ml of undiluted hybridoma supernatant.

By western blot, all of the antibodies are able to recognize full length, 48 kDa, GST-NAPC and full length trpE-NAPC. None recognize GST-hMDM2 or trpE-MAPC. They all, however, detect a number of lower molecular weight bands in the GST-NAPC lane. These bands are most likely caused by proteolytic degradation of full length GST-NAPC.

For immunoprecipitation, SW 480 cells were metabolically labeled with $^{35}$S-methionine. The lysate was then precipitated using 12 µg, in hybridoma supernatant, of each antibody. Five of the antibodies, BD12, CC1, CF11, EF4, and FE9 are able to detect the 147 kDa APC protein in SW 480 lysates by immunoprecipitation. See, e.g., FIG. 1C, lane 1. A summary of the characterization is presented in Table 1.

Example 5

This example demonstrates the detection of APC protein in seven lymphoblastoid and a colorectal cell line by monoclonal and polyclonal antibodies in Western blots.

Polyclonal and monoclonal antibodies were used for Western blot analysis of protein lysates from the colorectal cancer cell line SW480 and from seven EBV-immortalized lymphoblastoid lines generated from FAP patients. The SW480 cell line contains only one allele of the APC gene, and that allele has a nonsense mutation at codon 1338 resulting in a predicted protein size of 147 kDa (Nishisho, I., et al., Science 253:665–669 (1991)). All seven FAP cell lines contain a normal allele as well as a known truncating mutation of the APC gene (Miyoshi, Y. et al., Proc. Natl. Acad. Sci USA 89:4452–4456 (1992)).

The normal APC gene is predicted to encode a protein of 312 kDa while the mutations result in proteins with predicted relative sizes ranging from 27 kDa to 147 kDa. Analysis of protein lysates by standard Western Blot techniques following SDS-PAGE failed to detect full length APC protein. To facilitate detection of large proteins, protein lysates were subjected to electrophoresis through a denaturing agarose gel system and protein transfer was accomplished by capillary action. This transfer system coupled with enhanced chemiluminescence allowed detection of full length APC protein. More specifically, electrophoresis was performed in a 3% low melting point agarose gel formed in 0.1% SDS in Tris-borate buffer (89 mM Tris base, 89 mM boric acid, 2 mM EDTA), Trisglycine buffer (25 mM Tris base, 191 mM glycine, 0.05% SDS) was used as the running buffer. Cell protein lysates were prepared by boiling for five min in SDS-PAGE loading buffer (63 mM Tris-HCl, pH 6.8, 10% glycerol, 5% 2-mercaptoethanol, 2% SDS, 0.025% bromophenol blue). Protein concentrations were determined following Amido Black staining as previously described (Sheffield, J. N., et al., Analytical Biochemistry 166:49–54 (1987)) and 100 µg of total protein was loaded in each lane. The proteins were transferred by capillary action to a polyvinyldifluoride membrane (Immobilon, Millipore) in Tris buffered saline (0.1M Tris-HCl, pH 7.5, 0.9% sodium chloride) (TBS) with 0.04% SDS overnight. The filters were briefly rinsed with TBS and blocked with 10% nonfat dried milk, 10% goat serum, 0.1% Tween 20 in TBS for 1 hr. After incubation with 1–2 µg/ml of primary antibody in 5% nonfat dried milk, 0.1% Tween 20 in TBS for two hr, the filters were washed for 30 min in 0.1% Tween 20 in TBS with three changes. Horseradish peroxidase conjugated goat anti-rabbit or goat anti-mouse antibodies (0.05 µg/ml in 5% nonfat dried milk, 0.5% Tween 20 in TBS) were incubated with the filter for 45 min. The filters were then washed six times, 20 min. each, with 0.1% Tween 20 in TBS. Peroxidase activity was detected using Amersham's enhanced chemiluminescence detection kit following the manufacturer's protocol.

Figure 1B:
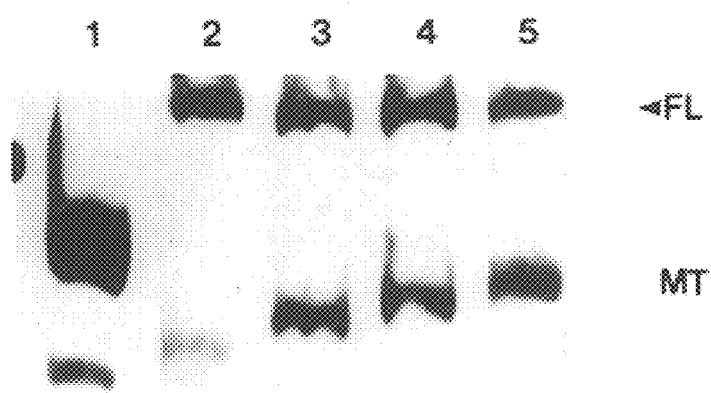
Figure 1C:
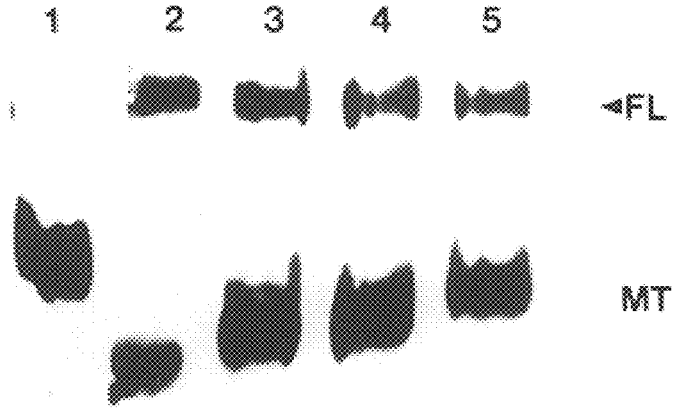

Polyclonal anti-NAPC, anti-MAPC and monoclonal FE9 antibodies all detected an approximately 300 kDa protein in the FAP cell lines which was absent in the SW480 cell line (examples in FIGS. 1A, 1B and 1C). Furthermore, truncated proteins corresponding to the expected sizes were detected in SW480 and four of the FAP lines (FIG. 1). In one case, freshly drawn blood was obtained from an FAP patient and peripheral mononuclear cells were isolated. Peripheral mononuclear cells were isolated from EDTA anticoagulated blood using an Histopaque 1077 step gradient (Sigma) following the manufacturer's protocol. Both mutant (117 kDa) and full length APC protein were detectable providing evidence that this analysis could be done directly on blood cells. In three of the FAP lymphoblastoid samples, truncated proteins were not detected, even though full length APC proteins were easily detectable (data not shown). These included lines with nonsense mutations at codons 232, 301 and 625. Three independent cell lysates from each of these cell lines were analyzed with anti-NAPC or FE9 using a variety of different gel electrophoresis conditions that should have allowed detection of proteins in the size range predicted by the mutations. These results suggest that certain forms of truncated APC are expressed at very low levels relative to full length, likely due to instability of the mutant transcript or protein.

Similar results were obtained with monoclonals FE9, CF11 and EF4. A fourth monoclonal CC1 failed to detect endogenous APC on Western blots even though CC1 was able to immunoprecipitate metabolically labelled endogenous APC (data not shown).

Example 6

This example demonstrates the use of antibodies specific for APC to detect altered APC protein in human tumor cell lines.

We determined the status of APC protein in human tumors. In order to avoid problems with contaminating normal tissue, we examined APC protein in human cell lines derived from colonic, breast, prostatic, cervical, lung and pancreatic tumors. A total of 32 colorectal tumor cell lines were studied including 6 derived from sporadic adenomas, 22 from sporadic carcinomas, 3 from FAP adenomas, and one from an FAP carcinoma. Western blot analysis revealed that 24 (75%) of these lines contained truncated APC protein (examples in FIG. 2). Cell lines were scored positive for truncated APC protein only if the novel band reacted with Anti-NAPC, Anti-MAPC, and FE9 antibodies. Interestingly, greater than 80% (27 of 32) of the colon lines were totally devoid of full length APC protein.

Figure 2:
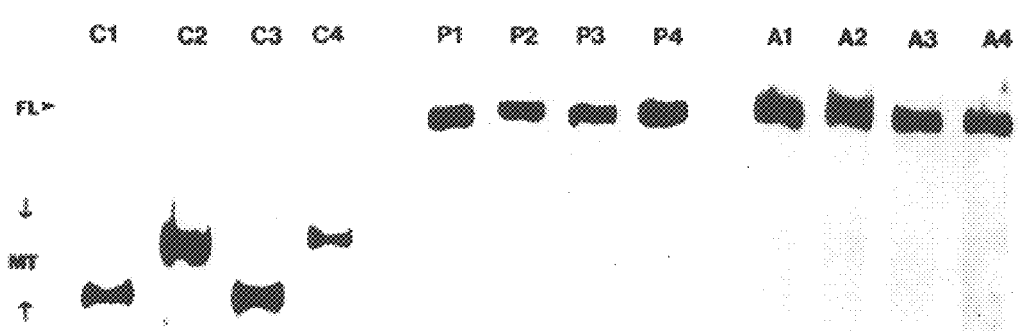
FIG. 2 displays the characterization of APC protein in tumor cell lines by Western blot analysis. Total protein lysates (100 µg) were assayed by Western blot with monoclonal FE9. Examples from one colon cancer (C1), three colon adenomas (C2 to C4), four prostatic cancers (lanes P1 to P4), and four pancreatic cancers (lanes A1 to A4) cell lines are shown. Full length protein is indicated as "FL" and mutant truncated protein is indicated as "MT". The truncated proteins migrate as 100, 130, 100, and 135 kDa polypeptides (left to right) as compared to standard molecular weight markers.

In contrast, seven breast, six prostatic, nine cervical, nine pancreatic and nine lung carcinoma cell lines each contained only full-length APC protein by Western blot analysis (examples in FIG. 2). The results suggest that APC mutations might not play a role in the development of these tumors, although it is possible that missense APC mutations and/or very early truncating mutations occur in these tumor types. These results also indicate that the APC protein is expressed at detectable levels in many different tissue types, specifically, lymphoid, lung, breast, prostate, pancreas and cervix.

Example 7

This example demonstrates that APC is localized to the cytoplasm.

Figure 3A:
FIGS. 3A and 3B illustrate the subcellular fractionation of normal and mutant APC protein. Cell lines were fractionated and each fraction was analyzed by Western blot using polyclonal Anti-APC antibodies.

Several experiments were undertaken to localize APC at the subcellular level. When cell fractionation using SW480 cells was performed, the truncated protein was found exclusively in the cytosolic fraction (FIG. 3A, lane 4). The procedure was performed as previously described (Sprott, et al., *Analytical Biochemistry*, 166:49–54 (1987)) with the following modifications. Cells were harvested by centrifugation at 200×g and washed three times with Dulbecco's phosphate buffered saline containing 0.5 mM calcium chloride. The pellet was resuspended in lysis buffer (5 mM Tris HCl, pH 7.8, 2 mM $MgCl_2$, 1 mM PMSF, 0.5 μg/ml leupeptin (Sigma), 10 μg/ml trypsin inhibitor (Sigma)). The sample was then centrifuged at 500×g to pellet nuclei and unlysed cells. The pellet was washed once with lysis buffer and saved as the "nuclear fraction". The supernatant was centrifuged at 100,000×g for 1 hr. The resulting pellet, was designated as the "membrane fraction", and the supernatant was designated the "cytosolic fraction". All three fractions were solubilized directly in SDS-PAGE loading buffer prior to Western blot analysis. These fractions were verified by finding that p53 and DCC were predominantly found in the "nuclear" and membrane" fractions, respectively.

Figure 3B:
Figure 3B:

When an FAP lymphoblastoid line containing full length and truncated APC protein was fractionated, the results were unexpected. The full-length APC protein was found in the 100,000×g insoluble "membrane fraction" while the truncated form was present in the 100,000×g fraction and in the cytosolic fraction (FIG. 3B, lane 2 and 4). APC fractionation was unaffected by Triton X-100 treatment but deoxycholate, a weak ionic detergent, completely solubilized full length and truncated APC (data not shown). This suggested that APC was not a membrane protein, but rather that the full length APC protein was complexed in an insoluble aggregate. This pattern of fractionation was reproduced with a second FAP lymphoblastoid line containing a different truncated APC protein.

To further define the subcellular localization of APC, immunohistochemical studies were performed on frozen normal colonic mucosa sections using affinity purified polyclonal antibodies. Frozen normal colonic mucosa samples were embedded in O.C.T. (Miles Laboratories, Inc.) and cut into 12 μm sections. The sections were immediately fixed in 0.3% hydrogen peroxide in absolute methanol at room temperature for 30 min. The tissues were washed three times in Dulbecco's phosphate buffered saline (PBS). The APC antigen was unmasked using the Antigen Retrieval System (Biogenex Laboratories) following the manufacturer's protocol. The tissues were briefly washed three times with $H_2O$ and three times with PBS, blocked with goat serum for 30 min, and then incubated with affinity purified Anti-NAPC (1.5 μg/ml) or Anti-MAPC antibodies (1.5 μg/ml) or normal rabbit immunoglobulins (4.5 μg/ml) diluted in goat serum for 2 hr. The tissues were washed with PBS three times for 5 min each. Biotinylated goat anti-rabbit antibody (Vector Laboratories) was diluted 1:200 in goat serum and exposed to the tissues for 30 min. The tissues were washed in PBS three times for five min. each. Immunoperoxidase staining was performed using the Vectastain Elite ABC System (Vector Laboratories) following the manufacturer's protocol. DAPI staining was performed as a nuclear counterstain by overlaying the immunoperoxidase stained tissue with 0.1 mg/ml DAPI and viewing under U.V. excitation. Competition studies were performed using soluble GST fusion proteins purified as previously described (Smith D. B., et al. *Gene* 67: 3–40, (1988)). GST-NAPC and GST-MDM2 fusion protein were included in the primary antibody incubations at a final concentration of 3 μg/ml and 9 μg/ml, respectively.

Figure 4A:
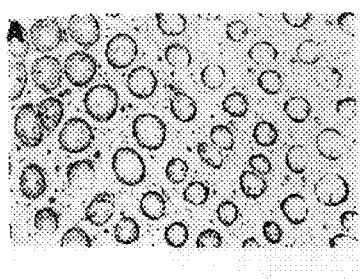
FIGS. 4A, 4B, 4C, 4D, 4E and 4F photographically capture immunohistochemistry of normal colonic mucosa using affinity purified polyclonal anti-NAPC antibodies. The pattern of staining with polyclonal anti-NAPC antibody (FIG. 4A, low power and FIG. 4B, medium power) is not seen with a three-fold higher concentration of normal rabbit immunoglobulin (FIG. 4D, low power and FIG. 4E, medium power). This signal was effectively competed with GST-NAPC (FIG. 4F, medium power) but was not competed with a three-fold higher concentration of GST-MDM2 (FIG. 4C, medium power).
Figure 4B:
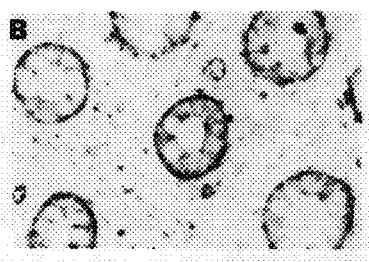
Figure 4C:
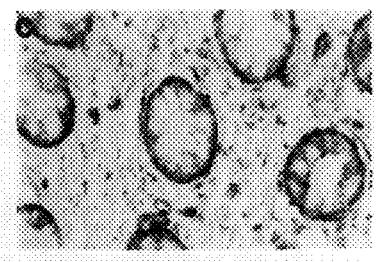
Figure 4D:
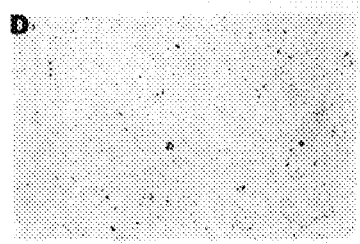
Figure 4E:
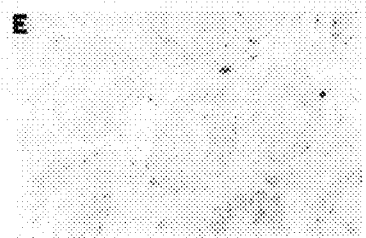
Figure 4F:
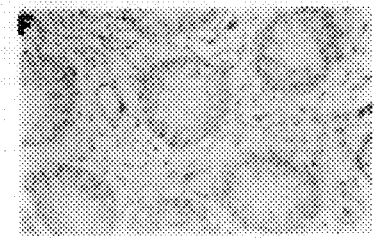

Cytoplasmic staining concentrated at the basolateral portion of crypt epithelial cells was seen with Anti-NAPC (FIGS. 4A and 4B), but not with a three fold higher concentration of normal rabbit IgG (FIGS. 4D and 4E). When counterstained with DAPI, the darkest APC specific staining was shown to be basolateral to the nuclei. The staining of epithelial cells displays a marked increase from the base of the crypt to the luminal surface. The identical pattern was observed with polyclonal Anti-MAPC antibodies. To confirm that this antibody binding was specific for APC, competitions were performed with soluble bacterial GST-NAPC fusion protein or a control unrelated fusion protein (GST-MDM2). The signal was fully competed by the NAPC fusion protein (FIG. 4F), but was unaffected by three-fold higher concentration of the MDM2 fusion protein (FIG. 4C). The signal seen with Anti-MAPC antibodies could not be competed away by soluble bacterial NAPC fusion protein, as expected. The same pattern of staining was observed in FAP colonic mucosa from two individuals with either a codon 625 or 1309 truncating mutation (data now shown).

We claim:

1. A method for determining the presence of a mutation in human APC gene which results in a truncated APC gene product, comprising:

extracting proteins from a tissue sample or body fluid of a human;

separating said extracted proteins on an agarose gel;

blotting said separated proteins onto a filter by means of capillary action;

contacting said filter with antibodies which are specifically immunoreactive with amino acids 16–29 of APC protein as shown in SEQ ID NO:2 to bind said antibodies to proteins blotted on said filter;

detecting the location on the filter of said antibodies which bind to said proteins;

determining the size of the proteins which are bound to said antibodies, wherein a size of less than about 300 kDa indicates the presence of an APC mutation which results in truncation of APC gene product in the tissue sample or body fluid.

2. The method of claim 1 wherein the antibodies are made by a cell line selected from the group consisting of FE9, CF11, CC1, and AC4 deposited at the ATCC as Accession Nos. HB 11294, HB 11288, HB 11296, and HB 11292, respectively.

3. The method of claim 1 wherein the antibodies are polyclonal.

4. The method of claim 1 wherein the antibodies are monoclonal.

5. The method of claim 1 wherein the tissue sample is a tumor.

6. The method of claim 1 wherein the body fluid comprises peripheral blood mononuclear cells.

7. A method for determining the presence of an APC mutation which results in a truncated APC gene product in a human, comprising the steps of:

contacting a first sample of a tissue or body fluid with a first antibody which is specifically immunoreactive with an epitope contained within amino acids 16–29 or 109–170 of APC protein as shown in SEQ ID NO:2;

determining the amount of binding of the first antibody to said first sample;

contacting a second sample of the tissue or body fluid with a second antibody which is specifically immunoreactive with an epitope contained within the carboxy terminal 306 amino acids of APC as shown in SEQ ID NO:2;

determining the amount of binding of the second antibody to said second sample;

comparing the determined amount of binding of said first antibody to the determined amount of binding of said second antibody, wherein finding a sample which binds substantially more of the first antibody than the second antibody indicates an APC mutation which results in a truncated APC gene product in the human.

8. The method of claim 7 wherein the first and second samples of the tissue comprise tumor tissue.

9. The method of claim 7 wherein the first and second samples of the body fluid comprise peripheral blood mononuclear cells.

10. The method of claim 7 wherein the first and second samples comprise a lysate of a tumor tissue.

11. The method of claim 7 wherein the first and second samples are the same sample and the first and second antibodies are labelled with different detectable tags.

12. The method of claim 7 wherein antibody binding is determined by means of a colored reaction product which is generated by an enzyme which is linked to an antibody selected from the group consisting of: said first antibody, said second antibody, an antibody which binds to said first antibody, and an antibody which binds to said second antibody.

13. The method of claim 7 wherein antibody binding is detected by means of a fluorescent compound which is linked to an antibody selected from the group consisting of: said first antibody, said second antibody, an antibody which binds to said first antibody, and an antibody which binds to said second antibody.

14. The method of claim 7 wherein the first antibody is secreted by a hybridoma selected from the group consisting of FE9, CF11, CC1, and AC4, which are deposited at the ATCC as Accession Nos. HB 11294, HB 11288, HB 11296, and HB 11292, respectively.

15. The method of claim 7 wherein the second antibody is selected from the group of antibodies secreted by the hybridomas HG2, DB1, IA1, and IE1, which are deposited at the ATCC as Accession Nos. HB 11293, HB 11295, HB 11297, and HB 11298, respectively.

16. The method of claim 7 which is an enzyme-linked immunosorbent assay (ELISA) method.

17. The method of claim 7 which is an immunohistochemical assay method.

18. A method for detecting truncated forms of APC by detecting a difference in subcellular localization, comprising the steps of:

lysing a test sample of cells from a human;

fractionating said lysed cells into a cytosolic and a membrane fraction;

contacting said cytosolic fraction with an antibody which is specifically immunoreactive with an epitope contained within the amino terminal 1103 amino acids of APC as shown in SEQ ID NO:2;

detecting any of said antibody which bound to said cytosolic fraction, the presence of antibody bound to the cytosolic fraction indicating a truncated form of APC in said cells.

19. The method of claim 18 further comprising the steps of:

contacting said membrane fraction with said antibody;

detecting any of said antibody which bound to said membrane fraction, the absence of antibody bound to the membrane fraction indicating the absence of any full length APC in said cells.

* * * * *